(12) United States Patent
Burnett et al.

(10) Patent No.: US 8,048,169 B2
(45) Date of Patent: Nov. 1, 2011

(54) PYLORIC VALVE OBSTRUCTING DEVICES AND METHODS

(75) Inventors: Daniel R. Burnett, San Francisco, CA (US); Gregory W. Hall, Redwood City, CA (US); Roxanne Richman, San Jose, CA (US); David A. Gallup, Alameda, CA (US); Annette Campbell-White, Oakland, CA (US)

(73) Assignee: BAROnova, Inc., Goleta, CA (US)

( * ) Notice: Subject to any disclaimer, the term of this patent is extended or adjusted under 35 U.S.C. 154(b) by 1400 days.

(21) Appl. No.: 10/833,950

(22) Filed: Apr. 27, 2004

(65) Prior Publication Data

US 2005/0033331 A1    Feb. 10, 2005

Related U.S. Application Data

(63) Continuation-in-part of application No. 10/671,191, filed on Sep. 24, 2003, now Pat. No. 6,994,095.

(60) Provisional application No. 60/525,105, filed on Nov. 26, 2003, provisional application No. 60/490,421, filed on Jul. 28, 2003.

(51) Int. Cl.
*A61F 2/04* (2006.01)

(52) U.S. Cl. .................................................. 623/23.65

(58) Field of Classification Search ................ 606/127, 606/151, 153, 200, 198, 191, 192, 108, 139, 606/213, 215, 216, 193, 194–197; 604/270, 604/523, 175, 516, 264, 96.01, 104–106, 604/8, 9, 43, 101.01, 101.05, 102.01, 246, 604/27, 14.13; 128/830, 831; 623/23.65, 623/1.24, 1.11, 23.64, 23.68
See application file for complete search history.

(56) References Cited

U.S. PATENT DOCUMENTS

| | | | |
|---|---|---|---|
| 4,133,315 | A | 1/1979 | Berman et al. |
| 4,246,893 | A | 1/1981 | Berson |
| 4,315,509 | A | 2/1982 | Smit |

(Continued)

FOREIGN PATENT DOCUMENTS

DE    4012642    10/1991

(Continued)

OTHER PUBLICATIONS

U.S. Appl. No. 10/671,191, filed Sep. 24, 2003 in the name of Burnett, Final Office Action mailed May 5, 2005.

(Continued)

*Primary Examiner* — S. Thomas Hughes
*Assistant Examiner* — Jocelin Tanner
(74) *Attorney, Agent, or Firm* — Levine Bagade Han LLP

(57) ABSTRACT

Methods, devices and systems facilitate intermittent and/or partial obstruction of a pyloric valve. Devices generally include a support portion for preventing the device from passing through the pyloric valve and a tissue engagement portion for contacting tissue adjacent the pyloric valve to obstruct the valve. Some embodiments also include a positioning member extending from the tissue engagement portion for helping position the device for obstructing the valve. A retaining member may optionally be included on the distal end of the positioning member for further maintaining a position of the device in the stomach. Some embodiments are deliverable into the stomach through the esophagus, either by swallowing or through a delivery tube or catheter. Some embodiments are fully reversible. Some embodiments self-expand within the stomach, while others are inflated or otherwise expanded.

44 Claims, 22 Drawing Sheets

U.S. PATENT DOCUMENTS

| | | | |
|---|---|---|---|
| 4,416,267 A | 11/1983 | Garren et al. | |
| 4,485,805 A | 12/1984 | Foster, Jr. | |
| 4,517,979 A | 5/1985 | Pecenka | |
| 4,657,020 A | 4/1987 | Lifton | |
| 4,694,827 A | 9/1987 | Weiner et al. | |
| 4,735,214 A | 4/1988 | Berman | |
| 4,836,204 A | 6/1989 | Landymore et al. | |
| 4,878,905 A | 11/1989 | Blass | |
| 5,011,488 A * | 4/1991 | Ginsburg | 606/159 |
| 5,108,420 A * | 4/1992 | Marks | 606/213 |
| 5,129,915 A | 7/1992 | Cantenys | |
| 5,192,301 A | 3/1993 | Kamiya et al. | |
| 5,282,829 A | 2/1994 | Hermes | |
| 5,306,300 A * | 4/1994 | Berry | 623/23.64 |
| 5,312,343 A * | 5/1994 | Krog et al. | 604/101.03 |
| 5,423,872 A | 6/1995 | Cigaina | |
| 5,509,888 A | 4/1996 | Miller | |
| 5,514,091 A | 5/1996 | Yoon | |
| 5,634,936 A | 6/1997 | Linden et al. | |
| 5,782,800 A | 7/1998 | Yoon | |
| 5,820,584 A | 10/1998 | Crabb | |
| 5,853,422 A | 12/1998 | Huebsch et al. | |
| 5,976,174 A | 11/1999 | Ruiz | |
| 6,067,991 A | 5/2000 | Forsell | |
| 6,102,928 A | 8/2000 | Bonutti | |
| 6,112,703 A | 9/2000 | Handelsman | |
| 6,117,159 A | 9/2000 | Huebsch et al. | |
| 6,152,144 A | 11/2000 | Lesh et al. | |
| 6,162,201 A | 12/2000 | Cohen | |
| 6,183,520 B1 | 2/2001 | Pintauro et al. | |
| 6,245,090 B1 * | 6/2001 | Gilson et al. | 606/213 |
| 6,270,515 B1 | 8/2001 | Linden et al. | |
| 6,371,974 B1 | 4/2002 | Brenneman et al. | |
| 6,409,656 B1 | 6/2002 | Sangouard et al. | |
| 6,488,962 B1 | 12/2002 | Berner et al. | |
| 6,527,701 B1 | 3/2003 | Sayet et al. | |
| 6,540,789 B1 | 4/2003 | Silverman et al. | |
| 6,544,291 B2 | 4/2003 | Taylor | |
| 6,558,400 B2 | 5/2003 | Deem et al. | |
| 6,600,953 B2 | 7/2003 | Flesler et al. | |
| 6,652,578 B2 | 11/2003 | Bailey et al. | |
| 6,675,809 B2 * | 1/2004 | Stack et al. | 128/898 |
| 6,689,046 B2 | 2/2004 | Sayet et al. | |
| 6,740,121 B2 | 5/2004 | Geitz | |
| 6,755,869 B2 | 6/2004 | Geitz | |
| 6,802,868 B2 | 10/2004 | Silverman et al. | |
| 6,994,095 B2 | 2/2006 | Burnett | |
| 7,011,621 B2 | 3/2006 | Sayet et al. | |
| 7,037,344 B2 * | 5/2006 | Kagan et al. | 623/23.65 |
| 7,054,690 B2 | 5/2006 | Imran et al. | |
| 7,087,072 B2 * | 8/2006 | Marino et al. | 606/213 |
| 7,120,498 B2 | 10/2006 | Imran et al. | |
| 7,122,058 B2 | 10/2006 | Levine et al. | |
| 7,146,984 B2 | 12/2006 | Stack et al. | |
| 7,160,312 B2 | 1/2007 | Saadat | |
| 7,167,750 B2 | 1/2007 | Knudson et al. | |
| 2002/0091395 A1 | 7/2002 | Gabbay | |
| 2002/0165589 A1 | 11/2002 | Imran et al. | |
| 2002/0188354 A1 | 12/2002 | Peghini | |
| 2002/0198470 A1 | 12/2002 | Imran et al. | |
| 2002/0198479 A1 | 12/2002 | Imran et al. | |
| 2003/0023150 A1 | 1/2003 | Yokoi et al. | |
| 2003/0040804 A1 | 2/2003 | Stack et al. | |
| 2003/0078611 A1 | 4/2003 | Hashiba et al. | |
| 2003/0093117 A1 | 5/2003 | Saadat | |
| 2003/0109931 A1 | 6/2003 | Geitz | |
| 2003/0109935 A1 | 6/2003 | Geitz | |
| 2003/0120328 A1 | 6/2003 | Jenkins et al. | |
| 2003/0144708 A1 | 7/2003 | Starkebaum | |
| 2003/0153806 A1 | 8/2003 | Miller | |
| 2003/0158601 A1 | 8/2003 | Silverman et al. | |
| 2004/0034408 A1* | 2/2004 | Majercak et al. | 623/1.15 |
| 2004/0107004 A1 | 6/2004 | Levine et al. | |
| 2004/0117031 A1* | 6/2004 | Stack et al. | 623/23.65 |
| 2004/0158331 A1 | 8/2004 | Stack et al. | |
| 2004/0172141 A1 | 9/2004 | Stack et al. | |
| 2004/0172142 A1 | 9/2004 | Stack et al. | |
| 2004/0230222 A1* | 11/2004 | van der Burg et al. | 606/213 |
| 2004/0236357 A1 | 11/2004 | Kraemer et al. | |
| 2005/0033332 A1 | 2/2005 | Burnett | |
| 2005/0055039 A1 | 3/2005 | Burnett et al. | |
| 2005/0090873 A1 | 4/2005 | Imran et al. | |
| 2005/0096673 A1 | 5/2005 | Stack et al. | |
| 2005/0192629 A1 | 9/2005 | Saadat et al. | |
| 2005/0273060 A1 | 12/2005 | Levy et al. | |
| 2006/0020278 A1 | 1/2006 | Burnett et al. | |
| 2006/0178691 A1 | 8/2006 | Binmoeller | |
| 2006/0282107 A1 | 12/2006 | Hashiba et al. | |
| 2006/0293742 A1 | 12/2006 | Dann et al. | |
| 2007/0016262 A1 | 1/2007 | Gross et al. | |
| 2007/0027548 A1 | 2/2007 | Levine et al. | |
| 2007/0083224 A1 | 4/2007 | Hively | |
| 2007/0135831 A1 | 6/2007 | Burnett et al. | |
| 2007/0178160 A1 | 8/2007 | Burnett | |
| 2007/0250132 A1 | 10/2007 | Burnett | |
| 2009/0118757 A1 | 5/2009 | Burnett et al. | |
| 2009/0118758 A1 | 5/2009 | Burnett et al. | |
| 2009/0182357 A1 | 7/2009 | Burnett et al. | |
| 2009/0182358 A1 | 7/2009 | Burnett et al. | |
| 2009/0187200 A1 | 7/2009 | Burnett et al. | |
| 2009/0187201 A1 | 7/2009 | Burnett et al. | |
| 2009/0198210 A1 | 8/2009 | Burnett et al. | |
| 2009/0216262 A1 | 8/2009 | Burnett et al. | |

FOREIGN PATENT DOCUMENTS

| | | |
|---|---|---|
| WO | WO 00/48672 | 8/2000 |
| WO | WO 02/091961 A1 | 11/2002 |
| WO | WO 03/017882 A2 | 3/2003 |
| WO | WO 2005/009288 | 2/2005 |
| WO | WO 2005/104989 | 10/2005 |
| WO | WO 2006/020370 | 2/2006 |
| WO | WO 2006/135857 | 12/2006 |
| WO | WO 2007/027812 | 3/2007 |
| WO | WO 2007/092390 | 8/2007 |
| WO | WO 2007/092501 | 8/2007 |
| WO | WO 2009/033049 | 3/2009 |

OTHER PUBLICATIONS

U.S. Appl. No. 10/671,191, filed Sep. 24, 2003 in the name of Burnett, Non-final Office Action mailed Dec. 15, 2004.

U.S. Appl. No. 10/671,191, filed Sep. 24, 2003 in the name of Burnett, Notice of Allowance mailed Sep. 13, 2005.

U.S. Appl. No. 10/915,716, filed Aug. 9, 2004 in the name of Burnett et al., Final Office Action mailed Mar. 19, 2009.

U.S. Appl. No. 10/915,716, filed Aug. 9, 2004 in the name of Burnett et al., Non-final Office Action mailed May 29, 2008.

U.S. Appl. No. 11/215,430, filed Aug. 29, 2005 in the name of Burnett et al., Final Office Action mailed May 28, 2008.

U.S. Appl. No. 11/215,430, filed Aug. 29, 2005 in the name of Burnett et al., Non-final Office Action mailed Feb. 13, 2009.

U.S. Appl. No. 11/215,430, filed Aug. 29.2005 in the name of Burnett et al., Non-final Office Action mailed Mar. 8, 2007.

International Patent Application No. PCT/US2005/026370 filed Jul. 25, 2005 in the name of Baronova, Inc., International Search Report and Written Opinion mailed Sep. 30, 2008.

International Patent Application No. PCT/US2007/003052 filed Feb. 5, 2007 in the name of Baronova, Inc., International Search Report and Written Opinion mailed Nov. 19, 2007.

International Patent Application No. PCT/US2007/003260 filed Feb. 5, 2007 in the name of Baronova, Inc., International Search Report and Written Opinion mailed Sep. 26, 2008.

International Patent Application No. PCT/US2008/075439 filed Sep. 5, 2008 in the name of Baronova, Inc., International Search Report and Written Opinion mailed Nov. 10, 2008.

International Patent Application No. PCT/US2006/033923 filed Aug. 29, 2006 in the name of Baronova, Inc., International Search Report and Written Opinion mailed Jan. 18, 2008.

International Patent Application No. PCT/US2004/023470 filed Jul. 20, 2004 in the name of Polymorfix, Inc., International Search Report and Written Opinion mailed May 27, 2005.

European Patent Application No. 04778818.7 filed Jul. 20, 2004 in the name of Burnett et al., Office Action mailed Oct. 5, 2009.

U.S. Appl. No. 10/915,716, filed Aug. 9, 2004 in the name of Burnett et al., Non-final Office Action mailed Dec. 8, 2009.
European Patent Application No. 05774631.5 filed Jul. 25, 2005 in the name of Burnett et al., Supplementary Partial European Search Report and Opinion mailed Dec. 1, 2009.
European Patent Application No. 05774631.5 filed Jul. 25, 2005 in the name of Burnett et al., Office Action mailed Mar. 16, 2010.
Canadian Patent Application No. 2,534,118 filed Jul. 20, 2004 in the name of Burnett et al., Office Action mailed Apr. 1, 2010.
European Patent Application No. 07763667.8 filed Feb. 5, 2007 in the name of Burnett, Search Report and Opinion mailed Dec. 23, 2009.
European Patent Application No. 07763667.8 filed Feb. 5, 2007 in the name of Burnett, Office Action mailed Apr. 12, 2010.
U.S. Appl. No. 11/702,840, filed Feb. 5, 2007 in the name of Burnett et al., non-final Office Action mailed Feb. 4, 2010.
Canadian Patent Application No. 2,620,859 filed Aug. 29, 2006 in the name of Burnett et al., Office Action mailed Apr. 20, 2010.
U.S. Appl. No. 12/351,686, filed Jan. 9, 2009 in the name of Burnett et al., non-final Office Action mailed Jul. 8, 2010.
Australian Patent Application No. 2004258968 filed Jul. 20, 2004 in the name of Baranova, Inc., Office Action mailed Feb. 10, 2011.
Australian Patent Application No. 2004258968 filed Jul. 20, 2004 in the name of Baranova, Inc., Office Action mailed Jan. 11, 2010.
Australian Patent Application No. 2005274132 filed Jul. 25, 2005 in the name of Baranova, Inc., Office Action mailed Mar. 22, 2010.
Australian Patent Application No. 2006284801 filed Aug. 29, 2006 in the name of Baranova, Inc., Office Action mailed Oct. 16, 2009.
Canadian Patent Application No. 2,534,118 filed Jul. 20, 2004 in the name of Baranova, Inc., Notice of Allowance mailed Jan. 24, 2011.
Canadian Patent Application No. 2,576,476 filed Jul. 25, 2005 in the name of Baranova, Inc., Office Action mailed Dec. 3, 2010.
Canadian Patent Application No. 2,620,859 filed Aug. 29, 2006 in the name of Baranova, Inc., Notice of Allowance mailed Feb. 4, 2011.
Japanese Patent Application No. 2006-521910 filed Jul. 20, 2004 in the name of Polymorfix, Inc., Office Action mailed Mar. 9, 2010.
U.S. Appl. No. 10/915,716, filed Aug. 9, 2004 in the name of Burnett et al., Final Office Action mailed Dec. 29, 2010.
U.S. Appl. No. 11/702,840, filed Feb. 5, 2007 in the name of Burnett, Final Office Action mailed Oct. 27, 2010.
U.S. Appl. No. 12/351,686, filed Jan. 9, 2009 in the name of Burnett et al., final Office Action mailed Mar. 11, 2011.
U.S. Appl. No. 12/351,705, filed Jan. 9, 2009 in the name of Burnett et al., Non-final Office Action mailed Sep. 29, 2010.
U.S. Appl. No. 12/352,497, filed Jan. 12, 2009 in the name of Burnett et al., Non-final Office Action mailed Dec. 23, 2010.
U.S. Appl. No. 11/215,430, filed Aug. 29, 2005 in the name of Burnett et al., Non-final Office Action mailed Mar. 23, 2011.
U.S. Appl. No. 12/434,594, filed May 1, 2009 in the name of Burnett et al., Non-final Office Action mailed Mar. 24, 2011.
U.S. Appl. No. 12/351,644, filed Jan. 9, 2009 in the name of Burnett et al., Non-final Office Action mailed Mar. 24, 2011.
U.S. Appl. No. 12/351,665, filed Jan. 9, 2009 in the name of Burnett et al., Non-final Office Action mailed Mar. 24, 2011.
U.S. Appl. No. 11/602,620, filed Nov. 20, 2006 in the name of Burnett, Non-final Office Action mailed Mar. 29, 2011.
Australian Patent Application No. 2007212473 filed Feb. 5, 2007 in the name of Baranova, Inc., Office Action mailed Apr. 20, 2011.
Australian Patent Application No. 2007212404 filed Feb. 5, 2007 in the name of Baranova, Inc., Office Action mailed May 2, 2011.
U.S. Appl. No. 11/702,840, filed Feb. 5, 2007 in the name of Burnett et al., Non-final Office Action mailed May 20, 2011.
U.S. Appl. No. 12/351,705, filed Jan. 9, 2009 in the name of Burnett et al., final Office Action mailed Jun. 9, 2011.
Japanese Patent Application No. 2007-525638 filed Jul. 25, 2005 in the name of Baranova, Inc., Office Action mailed Jan. 4, 2011.
European Patent Application No. 05774631.5 filed Jul. 25, 2005 in the name of Baranova, Inc., Office Action mailed Mar. 25, 2011.
Japanese Patent Application No. 2008-529243 filed Aug. 29, 2006 in the name of Baranova, Inc., Office Action mailed May 17, 2011.

* cited by examiner

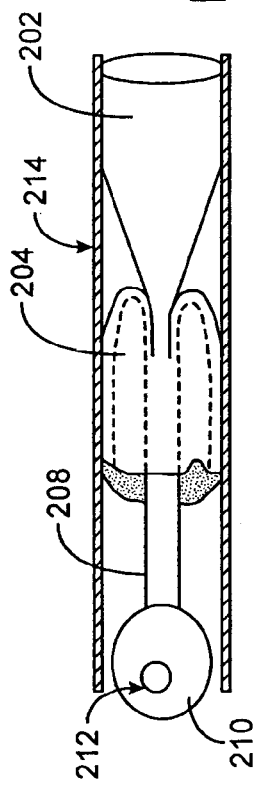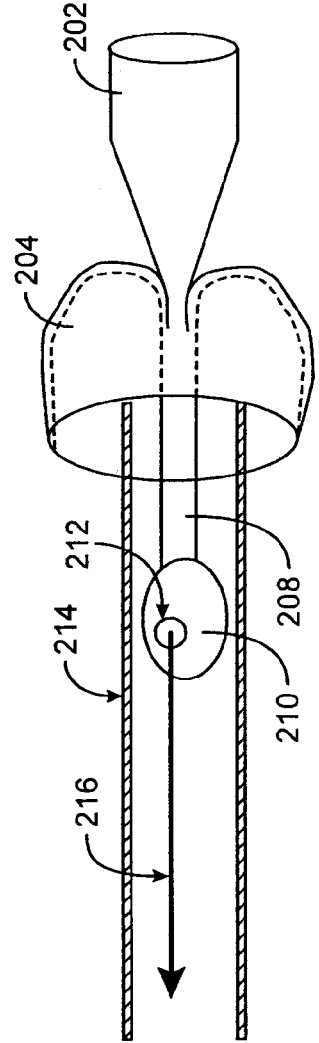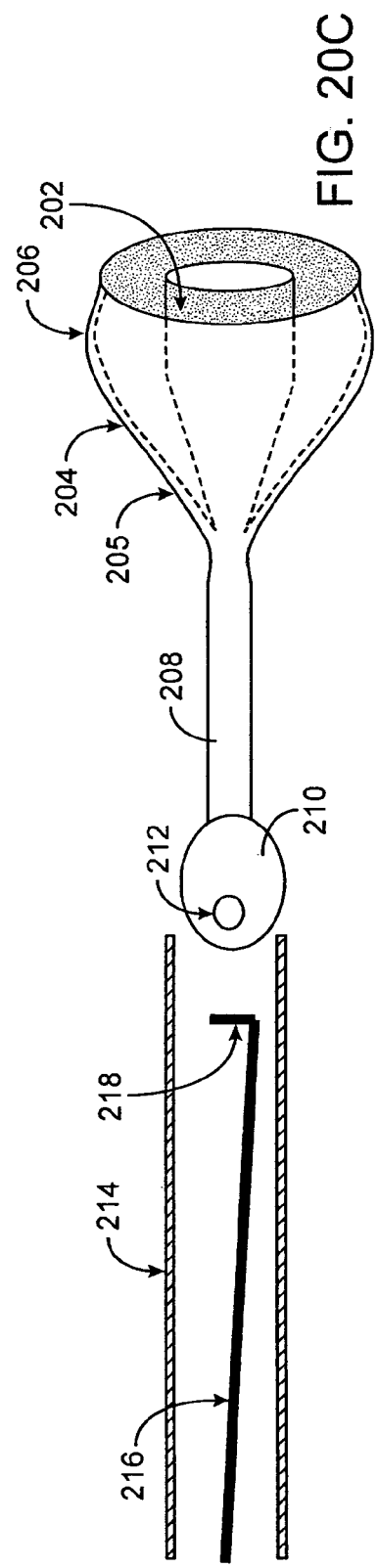

PYLORIC VALVE OBSTRUCTING DEVICES AND METHODS

CROSS-REFERENCES TO RELATED APPLICATIONS

This application is a continuation-in-part of U.S. patent application Ser. No. 10/671,191 filed Sep. 24, 2003, and entitled "Pyloric Valve Corking Device and Method," which claims priority to U.S. Provisional Patent Application Ser. No. 60/490,421, filed Jul. 28, 2003, and entitled "Pyloric Valve Corking Device and Method," the full disclosures of which are hereby incorporated by reference. This application also claims priority to U.S. Provisional Patent Application Ser. No. 60/525,105, filed Nov. 26, 2003, and entitled "Intragastric Therapeutic Device and Method," the full disclosure of which is hereby incorporated by reference.

FIELD OF THE INVENTION

The present invention relates generally to medical devices and methods. More specifically, the invention relates to devices and methods for partially and/or intermittently obstructing a pyloric valve to decrease gastric emptying, such as for treating obesity.

BACKGROUND OF THE INVENTION

Obesity has become a medical problem of epidemic proportions in the United States. Recent governmental studies estimate that as many as 40% of Americans are obese (defined as a Body Mass Index over 30), and of those, almost 20% are morbidly obese. Unfortunately, there is no indication that these percentages will decrease and every indication that they will increase in the coming years. Studies have linked obesity to countless health risks, a small sampling of which includes cardiovascular disease, cancer, diabetes, orthopedic injuries and complaints, obstructive sleep apnea, chronic fatigue and depression. Despite billions of dollars spent searching for obesity cures, conducting research into nutrition and exercise, and educating the public about obesity, efforts to date have been largely ineffective.

Many Americans have tried combating obesity with diet, exercise and even medications, to no avail. Most people who lose weight through diet and exercise gain it back again in a short period of time. Available medications can have serious side effects, as was evidenced by the recent scare with the Fen-Phen dietary medication. Faced with the difficultly of diet and exercise, nutritional information that seems to change radically and rapidly, and diet medications and supplements that typically do not work and may cause serious side effects, many obese people become frustrated and either decide to remain obese or choose to pursue a more drastic treatment option.

The more drastic options typically involve surgical procedures, such as stomach stapling, other gastric reduction surgical techniques, placement of a constrictive band around the outside of the stomach, and gastic bypass. The most well known procedure, in part due to well-publicized experiences of celebrities like Al Roker and Carney Wilson, is the gastric bypass operation, known technically as a Roux-En-Y gastric bypass. In this procedure, the stomach is actually bypassed, and a very small stomach-like pouch remains, making a patient feel full after ingesting a small amount of food. Although gastric bypass can be highly effective, it is acknowledged to be a very high-risk operation, with a 1-2% mortality rate, a number of possible complications such as digestive problems, and a recovery period of up to 6 months. The other surgical alternatives are also associated with either high risk, low rate of effectiveness, or both.

Stemming from the high risks of gastric surgical procedures and the ineffectiveness of diet and exercise for many obese people, a number of medical devices have been developed to address weight loss and obesity, but these too have numerous drawbacks. Some devices, for example, try to bypass a portion of the stomach or small intestine by essentially creating a tube or chute through which food passes without any nutrients or calories being absorbed. Such devices are described, for example, in U.S. Pat. No. 5,820,584 and U.S. Patent Application Publication Nos. 2003/0040804 and 2003/0109931. Unfortunately, these are designed to cause absorption problems in a patient, which may reduce intake of calories into the body but which also typically leads to "dumping" of food too rapidly through the digestive tract, leading to numerous gastrointestinal symptoms.

Another approach, as described for example in U.S. Patent Application Publication No. 2003/0093117, involves performing a minimally invasive surgical procedure on a stomach, typically to reduce its volume. The drawbacks with such approaches are that they are still relatively invasive and they are typically difficult or impossible to reverse.

Other techniques involve placing space-occupying balloons and other devices within the stomach to make the patient feel full after eating small amounts of food. One such a device, for example, is described in U.S. Patent Application Publication No. 2003/0109935. Space occupying devices by themselves, however, may not be as effective as other treatments, and many currently available devices have an unacceptably serious risk of collapsing, passing through the stomach, and lodging somewhere in the intestines, thus causing a serious and potentially fatal intestinal blockage.

Yet another technique that has been attempted for treating obesity involves slowing down the rate at which food passes from the stomach, through the pyloric valve at the distal end of the stomach, and into the duodenum—i.e., the first part of the small intestine. Some researchers have found, for example, that stimulation of the gastric vagus nerve may result in reduced gastric motility leading to a loss of over 20% of excess weight in a nine month period. In another approach, severing the gastric vagus nerve may also be effective in treating obesity. These therapies, however, require invasive, sometimes irreversible, surgical procedures, and may have adverse effects on the ability of the vagus nerve to perform other important functions.

Others have tried slowing gastric emptying by placing implants or injecting bulking agents into tissue at or immediately adjacent the pyloric valve. Such techniques are described, for example, in U.S. Pat. No. 6,540,789 and U.S. Patent Application Publication Nos. 2003/0153806 and 2003/0158601. In general, such methods have not been found to be effective and, again, are often irreversible.

Therefore, because obesity is such an endemic and serious health problem, and because currently available treatment options are often ineffective, extremely risky or both, a need exists for effective, relatively non-invasive treatments for obesity. Ideally, such treatments would be relatively easy to use and deploy in a patient and would help treat obesity without a high risk of side effects or severe complications. Such treatments would also ideally be reversible. At least some of these objectives will be met by the present invention.

SUMMARY OF THE INVENTION

The present invention provides devices, methods and systems for obstructing a pyloric valve to provide weight loss and in some cases treat or ameliorate obesity. Devices are generally delivered into the stomach where they expand or are expanded to partially and/or intermittently obstruct the pyloric valve. By partially or intermittently obstructing the pyloric valve, contents of the stomach (i.e., food) are retained longer in the stomach, thus causing a patient to feel full sooner and longer, and thus leading to reduced food intake and weight loss.

A device is generally configured such that, upon placement in the stomach, it moves naturally to the pyloric valve and contacts tissue adjacent the valve to obstruct the valve opening. A portion of the device is configured to assure that the device cannot pass through the pyloric valve and into the intestine, while another portion of the device is configured to contact stomach tissue adjacent the pyloric valve without damaging the tissue. During digestion and the natural contractions of the stomach, the device moves in and out of contact with the valve such that gastric contents are allowed to pass through to the small intestine, but the rate of passage is slowed. In a number of embodiments, a device may be introduced into the stomach either through a catheter device extending through the esophagus or by a patient swallowing the device. In some embodiments, the device may be retrieved and removed through the esophagus, often using the same device that was used for delivery. In other embodiments the obstructing device may dissolve over time and pass harmlessly through the digestive tract.

In one aspect of the present invention, a device for obstructing a pyloric valve of a stomach includes an expandable support portion adapted to expand in the stomach from a first configuration to a larger second configuration, and a compliant tissue engagement portion coupled with the expandable support portion and adapted to engage stomach tissue adjacent the pyloric valve to at least intermittently obstruct the pyloric valve. In the second configuration, the support portion prevents passage of the device through the pyloric valve. In general, the support portion and the tissue engagement portion may have any of a number of different configurations. In one embodiment, the two portions are part of one, unitary extrusion, with the support portion having a greater wall thickness than the tissue engagement portion and/or containing one or more support members, such as support rings, lattices, frames or the like. In other embodiments, the two portions may be separate pieces coupled together. The compliant tissue engagement portion generally is sufficiently compliant so as to prevent or avoid injury (such as erosion) of stomach tissue with which the device comes in contact.

In some embodiments, though not in all, the expandable support portion is self-expanding, thus including at least one self-expanding material. For example, the self-expanding material may include but is not limited to Nitinol, spring stainless steel or other shape-memory, super-elastic or spring-loaded materials. In some embodiments, the self-expanding material includes at least one support member, such as but not limited to one or more rings, coils, cages, struts, scaffolding, baskets, spokes or umbrellas. Such support members may be configured such that, once expanded, they prevent the device from collapsing and passing into the intestine. In some embodiments, the support portion includes one or more support members coupled with at least one material, such as of Gore-tex®, silicone, polyurethane or polyethylene. The tissue engagement portion, in turn, may extend from the support portion and be made of the same or different material, such as those just listed.

In alternative embodiments, the self-expanding material may include a self-expanding foam disposed within the expandable support portion and possibly the tissue engagement portion as well. For example, the foam may comprise polyethylene foam, polyurethane foam, silicone foam or the like. Like the support members just described, the expandable foam helps prevent passage of the device through the pyloric valve. Optionally, in some embodiments, the self-expanding material expands upon contacting one or more substances naturally present in the stomach.

In some embodiments, the support portion and the tissue engagement portion comprise at least one of Gore-tex®, silicone, polyurethane and polyethylene, with the wall thickness of the support portion being greater than the wall thickness of the tissue engagement portion. In such a device the support portion may also include one or more support members, such as Nitinol rings or the like. In some embodiments, the tissue engagement portion is adapted to temporarily form a seal with the pyloric valve upon contacting the tissue adjacent the valve, and the tissue engagement portion is sufficiently compliant to avoid causing damage to the tissue on contacting it.

In various embodiments, the obstruction device may have any suitable dimensions, configurations or the like. In one embodiment, for example, the support portion in the second configuration has a widest cross-sectional diameter of between 2.5 cm and 15 cm. The support portion and tissue engagement portion, in one embodiment, have a combined volume in the second configuration greater than 200 cc. This combined volume, in some embodiments, is sufficient to allow the device to act as a space occupying device (as well as a pyloric valve obstructing device) for treating obesity. In addition to its dimensions, the specific gravity or buoyancy of the device may enhance its ability to contact and obstruct the pyloric valve. In one embodiment, for example, the device has a specific gravity of between 0.25 and 4.0. Some embodiments may include one or more chambers for introducing a gas or fluid to adjust the buoyancy of the device, or other mechanisms for adjusting buoyancy.

As mentioned, the support portion and tissue engagement portion may have any suitable shape in various embodiments. In some embodiments, for example, the device may have an overall cross-sectional shape of a circle, ellipse, triangle, diamond, rectangle, square, star, combinations thereof or the like. In one embodiment, for example, the device may have an oblong or tubular shape. In some embodiments, the device is hollow, with one or more openings to allow passage of stomach contents in and out of the hollow portion. In another embodiment, the device is cone-shaped, with the tissue engagement portion disposed toward an apex of the cone and the support portion disposed toward a base of the cone. Another embodiment may be shaped like a cup. As will be described further below, a number of suitable alternatives is possible in various embodiments.

Some embodiments of the device also include a positioning member extending from the tissue engagement portion and having a shape adapted to pass at least partially through the pyloric valve to position the device over the pyloric valve. In one embodiment, the device further includes an inner plug and a compliant outer shell. The shell is movable from a first configuration in which it overlaps at least part of the positioning member to a second configuration in which it overlaps at least part of the plug. In this embodiment, the plug and a first portion of the shell in the second configuration act as the support portion, and a second portion of the shell in the second configuration acts as the tissue engagement portion. In one embodiment, the shell in the second configuration is generally cone-shaped. The outer shell may be made of any suitable material(s), but in one embodiment it comprises a material such as Gore-tex®, silicone, polyurethane or polyethylene, with the wall thickness of the first portion being greater than the wall thickness of the second portion. The thicker first portion provides some of the support function, while the thinner second portion provides the tissue engagement function. In some embodiments, the outer shell is movable from the first configuration to the second configuration by applying force to the shell with a distal end of an elongate catheter device. Also in some embodiments, the inner plug may be solid and may have a largest cross-sectional diameter of at least 10 mm.

Some of the embodiments including a positioning member may further include a retaining member coupled with a distal end of the positioning member for maintaining the device in intermittent contact with the pyloric valve. In some embodiments, the retaining member self-expands from a first configuration to a second configuration. Such a self-expanding retaining member may expand within the stomach or within the duodenum, in various embodiments. In some embodiments, the retaining member and the obstructing member are in fluid communication through the positioning member. A cross-sectional diameter of the retaining member may be either smaller or larger than a cross-sectional diameter of the support portion in the second configuration, according to various embodiments.

In various embodiments, the retaining member may include any of a number of different features. For example, in one embodiment the retaining member includes at least one hole, ring, loop or other surface feature for attaching a removal device, for removing the obstructing device from the stomach. In one embodiment, the retaining member includes at least one radiopaque marker or material for facilitating visualization of the device. In some embodiments, the retaining member is adapted to deliver at least one therapeutic or diagnostic agent to an intestine distal to the pyloric valve. For example, the retaining member may include a degradable material carrying the therapeutic or diagnostic agent. Alternatively, the retaining member may include one or more housings for releasably containing the therapeutic or diagnostic agent. In other embodiments, the therapeutic or diagnostic agent comprises a coating over at least part of the retaining member. In some embodiments, the retaining member includes an imaging device for imaging an intestine distal to the pyloric valve. The retaining member may also include a chemical measuring device for measuring levels in an intestine of at least one of lipids, sugars, alcohols, drugs, pH levels, pancreatic secretions, biliary secretions and/or other dietary or physiological chemicals.

A retaining member and/or a positioning member having certain dimensions may be advantageous in various embodiments. For example, in one embodiment a retaining member has a cross-sectional diameter of between 0.5 cm and 3.0 cm. In some embodiments, the positioning member has a length of at least 3.0 cm. In some embodiments, the positioning member has a cross-sectional diameter of 2 cm or less. The positioning member may have a general shape adapted to permit the device to intermittently move into and out of contact with the pyloric valve, such as a cylindrical shape or the like. In some embodiments, the positioning member is adapted to self-expand from a first diameter to a larger second diameter within the pyloric valve. In some embodiments, a distal end of the positioning member is weighted.

In a number of embodiments, the device is deliverable into the stomach through an esophagus with the support portion in the first configuration. In some embodiments, for example, a biodegradable covering is disposed over at least the support portion, the covering being adapted to constrain the support portion in the first configuration for delivery into the stomach and to degrade in the stomach to release the support portion from constraint. Whether including such a cover or not, in some embodiments the device is adapted to be swallowed by a patient with the support portion in the first configuration. Such a swallowed device may further include a retaining cord removably coupled with the device and adapted to extend from the device through the patient's esophagus to the patient's mouth. The cord may retain the device in the stomach until it expands from a first configuration to a second configuration, and then may be removed to allow the obstructing device to contact the pylorus. Optionally, the cord may provide for removal of the device if it does not properly deploy in the stomach. In some cases, the cord may be swallowed and may dissolve in the patient's stomach.

In other embodiments, the device may removably couplable with an endoscope, an orogastric tube or any other suitable elongate delivery device for delivery of the device to the stomach through the esophagus. In some embodiments, the device is adapted to be delivered through a lumen of a tube extending from the mouth through the esophagus into the stomach. Optionally, the support portion may be collapsible from the second configuration to the first configuration for removal of the device through the esophagus. Alternatively, the device may comprise one or more biodegradable materials so as to degrade over time and pass through the pyloric valve and the rest of a digestive system. Such biodegradable materials may include but are not limited to cellulose, polyethylene glycol, collagen, polylactic acid and/or other polymers.

The device as a whole may include any of a number of various features in various embodiments. For example, in one embodiment the support portion and/or the tissue engagement portion may include one or more radiopaque materials, dyes and/or markers. One embodiment may further include one or more therapeutic or diagnostic agents releasably coupled with the device for release within the stomach. Optionally, some embodiments include an imaging device coupled with the obstructing device for imaging the stomach, the pyloric valve, and/or the intestine distal to the pyloric valve. Some embodiments may include a chemical measuring device coupled with the obstructing device for measuring levels in the stomach of lipids, sugars, alcohols and/or the like. Some embodiments may include a space occupying member coupled with the obstructing device for occupying space in the stomach to treat obesity. Some embodiments may include one or more electrodes coupled with the device and removably attachable to stomach tissue. In such embodiments, a power source for applying energy to the electrodes, as well as other features, may be housed within the device. Electrodes may be coupled with the device via one or more cords or tethers.

In another aspect of the invention, a device for obstructing a pyloric valve of a stomach comprises an obstructing member adapted to expand in the stomach from a first configuration to a larger second configuration and a positioning member extending from the obstructing member. As described above, the positioning member has a shape adapted to pass at least partially through the pyloric valve to position the obstructing member over the pyloric valve. In some embodiments, the obstructing member self-expands from the first configuration to the second configuration.

In some embodiments, the obstructing member comprises an inner plug and a compliant outer shell. The shell is movable from a first configuration in which it overlaps at least part of the positioning member to a second configuration in which it overlaps at least part of the plug. The plug and a first portion of the shell in the second configuration act as the support portion, and a second portion of the shell in the second configuration acts as the tissue engagement portion. The inner plug and outer shell may have any of the features already described. The device as a whole may also have any of the features described above, in various embodiments. For example, some embodiments further include a retaining member as previously described.

In another aspect of the invention, a system for obstructing a pyloric valve of a stomach includes a pyloric valve obstructing device and a delivery device for delivering the pyloric valve obstructing device to the stomach through the esophagus. The pyloric valve obstructing device includes an expandable support portion adapted to expand in the stomach from a first configuration to a larger second configuration and a compliant tissue engagement portion coupled with the expandable support portion and adapted to engage stomach tissue adjacent the pyloric valve such that the device at least intermittently obstructs the pyloric valve. This obstruction device may optionally be self-expanding and may include any of the other features described above in various embodiments.

In some embodiments, the delivery device comprises an elongate flexible catheter. For example the flexible catheter may comprise an endoscope, an orogastric tube or the like in various embodiments. In some embodiments, the flexible catheter defines a lumen in which the obstructing device is housed during delivery. Such a flexible catheter may optionally further include a coupling mechanism for releasably holding the obstructing device within the lumen during delivery. The delivery device may also be adapted to remove the obstructing device from the stomach through the esophagus, in some embodiments. In an alternative embodiment, the device may be delivery in a collapsed state alongside an endoscope.

In alternative embodiments, the delivery device comprises a biodegradable caplet for containing the obstructing device to allow it to be swallowed by a patient, the biodegradable caplet dissolving within the stomach. In these or other embodiments, the obstructing device may comprise one or more biodegradable materials so as to degrade over time and pass through the pyloric valve and the rest of a digestive system. Such biodegradable materials may include but are not limited to cellulose, polyethylene glycol, collagen, polylactic acid and/or other polymers.

In some embodiments, the system further includes a space occupying member coupled with the obstructing device for occupying space in the stomach to treat obesity.

In another aspect of the present invention, a method for obstructing a pyloric valve of a stomach involves delivering a pyloric valve obstructing device through an esophagus to the stomach and releasing the obstructing device in the stomach to allow it to expand from a first configuration to a larger second configuration. As has been described above, the obstructing device in the second configuration is adapted to at least intermittently contact and obstruct the pyloric valve.

In some embodiments, releasing the obstructing device involves releasing the device from constraint to allow it to self-expand from the first configuration to the second configuration. For example, the obstructing device may be delivered to the stomach via an elongate flexible catheter, tube or scope advanced through an esophagus. In other embodiments, releasing the obstructing device involves allowing a patient to ingest the obstructing device in its first configuration. In some embodiments, for example, the device may be folded or compressed for swallowing, with the device unfolding or expanding upon arrival in the stomach. In another embodiment, delivering the device involves allowing the patient to ingest a biodegradable capsule containing the obstructing device in the first configuration, the biodegradable capsule degrading in the stomach to allow expansion to the second configuration.

Although some methods involve releasing a self-expanding obstructing device, other embodiments may involve actuating the expansion, using one or more delivery devices. For example, in some embodiments the method further involves inflating the obstructing device within the stomach before releasing it. Further details of inflatable obstructing devices and methods for their use can be found in U.S. patent application Ser. No. 10/671,191, of which the present application is a continuation-in-part and which was previously incorporated by reference. In alternative embodiments, the method may further involve moving an expandable shell of the obstructing device from a first position to a second position to expand the obstructing device from its first configuration to its second configuration. For example, in one embodiment the shell may be invert from a position facilitating delivery of the device to a position for obstructing the pyloric valve, using a distal end of a catheter delivery device. In some methods, it may also be possible to adjust buoyancy of the obstructing device before or after releasing it to allow it to migrate naturally within the stomach to contact and obstruct the pyloric valve. Adjusting the buoyancy, for example, might involve introducing a fluid or a gas into one or more chambers of the device.

In many, if not all, embodiments, delivery of an obstructing device is reversible. Reversibility may be achieved by a number of different techniques. In one embodiment, for example, the method for obstructing the pyloric valve further involves collapsing the obstructing device from the second configuration to the first configuration and removing the obstructing device from the stomach through the esophagus. An alternative embodiment involves cutting the obstructing device into multiple pieces and removing the obstructing device from the stomach through the esophagus. In either of these embodiments, the delivering, releasing, collapsing and removing steps may in some cases be achieved via one or more elongate flexible catheters, tubes or scopes advanced through an esophagus. In other embodiments, releasing the obstructing device in the stomach causes the device to begin to degrade. In such embodiments, reversibility is achieved by the device degrading over time and passing harmlessly through the digestive tract.

In some embodiments, the method further includes maintaining the obstructing device in at least intermittent contact with the pyloric valve by providing the device with a portion that extends at least partially through the pyloric valve. In some embodiments, a first portion of the obstructing member expands from the first configuration to the second configuration in the stomach, and a second portion of the obstructing member passes through the pyloric valve into adjacent intestine before expanding from the first configuration to the second larger configuration. Optionally, a bridging portion may extend between the first and second portions, through the pyloric valve, which may expand within the stomach or the pyloric valve.

The method may include additional features, such as visualizing at least one radiopaque marker or material of the obstructing device. In some embodiments, multiple radiopaque markers may be used to visualize the orientation of the device. In some case, the entire device is made of a radiopaque material. In another embodiment, the method includes acquiring one or more images of the stomach, the pyloric valve and/or the intestine, using an imaging device coupled with the obstructing device. In some embodiments, the obstructing member has a size in its second configuration that is sufficiently large as to act as a space-occupying device for further treating obesity. In other embodiments, the method may further involve expanding a space-occupying member coupled with the obstructing member within the stomach to further treat obesity.

In yet another aspect of the present invention, a method for obstructing a pyloric valve of a stomach involves passing a pyloric valve obstructing device in a first configuration through a lumen of an elongate catheter device extending through an esophagus to the stomach, advancing the obstructing device at least partially out of a distal end of the catheter device, and expanding the obstructing device from the first configuration to a second larger configuration using the catheter device. In one embodiment, for example, expanding the obstructing device involves inverting a compliant shell covering part of the device from a first, collapsed configuration to a second, expanded configuration, using a distal portion of the catheter device. Optionally, the method may further involve releasing the obstructing device from the catheter device.

These and other aspects and embodiments of the present invention are described in further detail below, with reference to the drawing figures.

BRIEF DESCRIPTION OF THE DRAWINGS

FIGS. 20A to 20C illustrate a method for delivering and deploying the device of FIGS. 19A and 19B.

DETAILED DESCRIPTION OF THE INVENTION

Figure 1A:
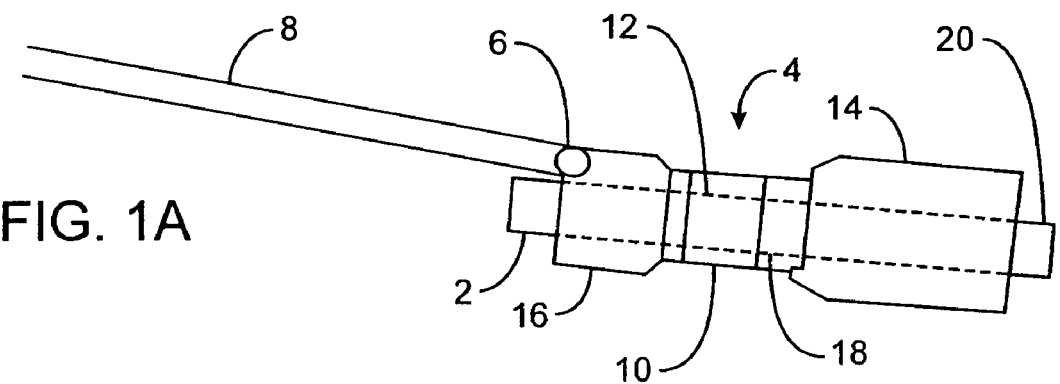
FIGS. 1A to 1C show cross-sectional views of one variation of a pyloric corking device designed to partially and/or intermittently obstruct a gastric opening in an unexpanded, partially unexpanded, and fully expanded configuration, respectively.
Figure 1B:
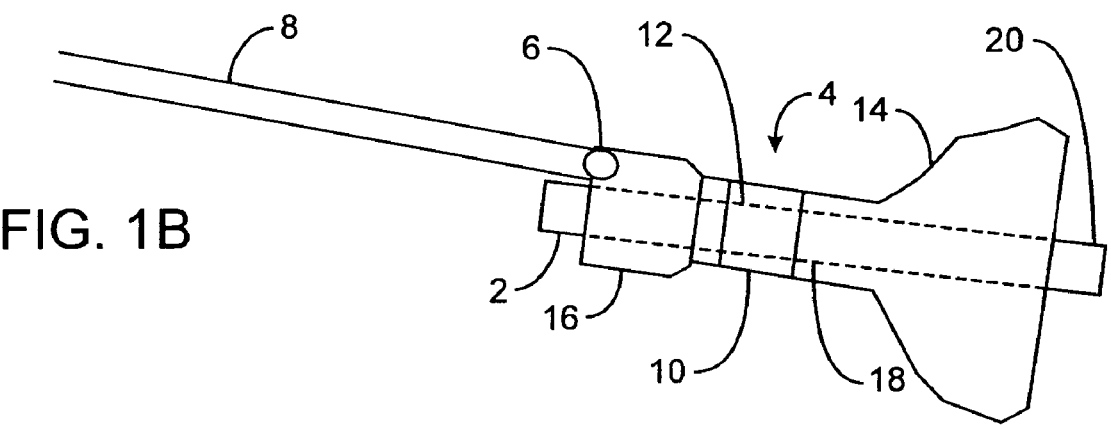
Figure 1C:
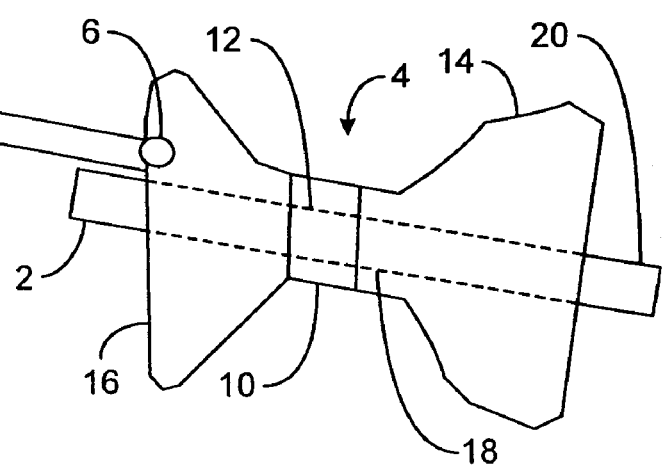

FIGS. 1A to 1C are cross-sectional views showing the expansion, respectively, of one variation of a pyloric corking device which is designed to partially and/or intermittently obstruct a gastric opening, particularly the pyloric valve. In this particular variation, FIG. 1A illustrates the device 4 in an unexpanded or uninflated state and ready for delivery and/or insertion into the pyloric valve. FIG. 1B shows the distal occlusion member 14 in an expanded state. In use, once the device 4 has been placed, e.g., in the pyloric region or beyond, the distal occlusion member 14 (or "retaining member") may be inflated through the influx of any number of biocompatible fluids or gases, e.g., saline, water, air, nitrogen, etc., through the tubing 8 leading to the inflation port 6, which may be self-sealing. Tubing 8 may include any number of delivery tubes such as catheters, endoscopes, etc.

The distal occlusion member 14 may be configured to inflate before the inflation of proximal occlusion member 16 by fabricating the inflatable member of distal occlusion member 14 with a material which is more easily distensible relative to a material of the proximal occlusion member 16. Materials which may be used in fabricating the occlusion members 14, 16 may include any number of materials such as silicone, silicone elastomers, latex, polyurethane, PTFE, FEP, etc. Alternatively, self-expanding materials, such as foam or hydrogels which typically expand upon contact with fluids, may be utilized within the occlusion members 14, 16. If such self-expanding materials are utilized, they may be disposed in the occlusion member 14, 16 and a fluid such as saline, may be infused to expand the materials. Different self-expanding materials may be incorporated in the distal occlusion member 14 than in the proximal occlusion member 16 to obtain differing radial pressures exerted by the expanding materials.

In yet another alternative, an expanding scaffolding may be utilized within each of the occlusion members 14, 16. Such a scaffold may be made of a shape memory alloy or superelastic alloy, such as Nitinol. The scaffold may be compressed into a delivery configuration and then either allowed to expand into the desired occlusive shape by self-expansion or by supplying an activation energy, e.g., electrical, heat, RF energy, etc. In either case, the distal occlusive member 14 may be positioned distal of the pyloric valve and then inflated or expanded into its larger configuration. It may then be pulled proximally against the pyloric annulus, at which point proximal occlusive member 16 may be inflated or expanded by infusion through port 6, as shown in FIG. 1C. With both occlusion members 14, 16 inflated or expanded, bridging member 10 connecting the two may span the pylorus. Bridging member 10 may be of various diameters, such as 1 mm and less, which does not significantly obstruct the pyloric sphincter, up to 8-10 mm in diameter, which does typically obstruct the pyloric sphincter, or any other suitable diameter.

Bridging member 10 may be designed to have a flexible length sufficient to allow the occlusion members 14, 16 to maintain its position with respect to the pyloric valve yet still enable the members 14, 16 to move. Proximal occlusion member 16 may move from fully obstructing the pyloric valve to moving proximally of the pyloric valve to the extent that distal occlusion member 14 allows member 16 to move. This movement may be elicited by the natural movements of the gastric lumen (stomach) and muscles surrounding the pyloric valve. Thus, when proximal occlusion member 16 is moved proximally, the pyloric valve is only partially obstructed and may allow for the intermittent passage of food between the bridging member 10 and the valve. Because any food within the stomach is retained for longer periods of time, feelings of satiation may be initiated sooner and prolonged so that the patient consumes less food. Moreover, to allow for the relative movement of the occlusion members 14, 16, bridging member 10 may be of a length which is sufficient to allow for its placement through the pyloric valve (or through another gastric opening) such that there is sufficient tolerance for the occlusion members 14, 16 to move proximally and distally relative to the pyloric valve. For instance, in the event that a patient's pyloric valve extends about 2 cm in length, the bridging member 10 is preferably longer than 2 cm, for example, up to 8 cm in length. Moreover, while occlusion members 14, 16 are inflatable or expandable, bridging member 10 itself may be configured to inflate or expand in diameter.

A visible dye or marker, preferably being highly visible, may optionally be infused into one or both of the occlusion members 14, 16 to function as a safety measure. Alternatively, one or both of the occlusion members 14, 16 may optionally be fabricated from a material which is highly visible and visually distinct from tissue so that in the unlikely event of an occlusion member 14, 16 rupturing, the dye or pieces of the occlusion member 14, 16 may become visible once passed from the body. This may indicate to the patient or physician that a rupture of the device has occurred.

Another variation may incorporate slow-releasing drugs infused into the materials covering the device or materials incorporated into the device. These drugs, which may be any number of drugs, may slowly infuse into the patient by drug release into the intestinal tract or through contact with the patient. Alternatively, the devices may incorporate electrical stimulation technologies. For instance, electrical probes may extend from a surface of the device for insertion into the surrounding tissue or electrodes may be formed over a surface of the device instead.

In yet another alternative, the occlusion members 14, 16 may be covered by an erodable or biodegradable covering over one or both members 14, 16. Such a covering may be configured to constrain one or both members 14, 16 and once the device has been ingested or placed within the gastric lumen, contact with the surrounding fluids may naturally erode the covering thus allowing the covered occlusion member to expand or inflate. In another variation, proximal and distal occlusion members may each be covered by different materials each configured to erode at differing rates or in different environments, as described in further detail below.

In the variation shown in FIGS. 1A to 1C, the device 4 may include an optional lumen 18 defined through the device 4. Optional lumen 18 may allow for the passage of fluids and food through the device 4 entering the lumen 18 through entry port 2 and exiting through the exit port 20. The lumen 18 may be designed to allow for the passage of a reduced volume of food through the device 4, in which case the device 4 shown may be configured with a relatively shortened bridging member 10 to inhibit the relative movement of the device 4 relative to the pylorus. With this variation, the lumen 18 has been configured so that it may be capable of actively pumping or metering the contents of the gastric lumen 74 into the intestine 76 through the device 4. In such a case, the need for the device 4 to be able to move to un-occlude the pyloric valve is removed. As shown in the figures, an optional pump or active metering valve 12 may be incorporated into the device 4. Pump or valve 12 may be configured to simply open and allow for the passage of the stomach contents through lumen 18 and valve 12 upon sensing the presence of foreign objects, such as food, in the stomach or upon sensing a predetermined pressure from the contents. Other sensing parameters may include temperature and pH levels. Alternatively, the pump or valve 12 may be configured to actively pump the stomach contents through the lumen 18 via a pumping mechanism automatically activated by pump or valve 12 or externally activated by the patient or physician through wireless communication. In the case where the device is configured with a valve 12, the valve may be configured as a unidirectional valve to allow the flow of fluids and food only from the stomach to the intestinal tract.

Figure 2A:
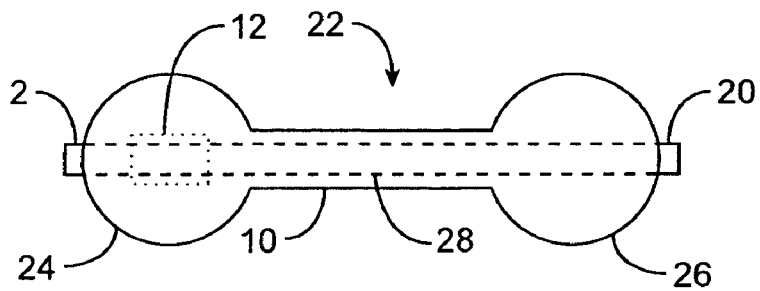
FIGS. 2A to 2D show side views of variations of the device utilizing occlusion members of different shapes.

The device 4 could have any shape provided that the shape and/or total volume of the proximal occlusion member 16 is sufficient to prevent its passage through the pyloric valve and into the intestines. FIGS. 2A to 2D show side views of different shape variations which are possible for use as occlusion members. For instance, FIG. 2A shows a side view of a device variation 22 in which proximal and distal occlusion members 24, 26 have a cross-sectional shape along a longitudinal axis defined by the device 22 in the form of circles, to form spherical occlusion members. Although proximal and distal occlusion members 24, 26 are illustrated having equally sized diameters, the diameters may be varied depending upon the desired shape and device configuration. For instance, proximal occlusion member 24 may be configured to have a diameter larger than distal occlusion member 26. Alternatively, a device having the opposite configuration may also be utilized, although this may be less preferable. Lumen 28 and pump or valve 12 may be optionally included, again depending upon the desired device configuration.

Figure 2B:
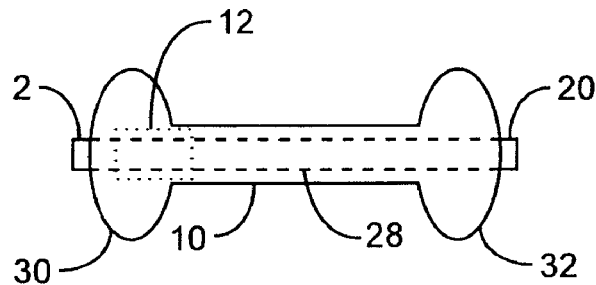
Figure 2C:
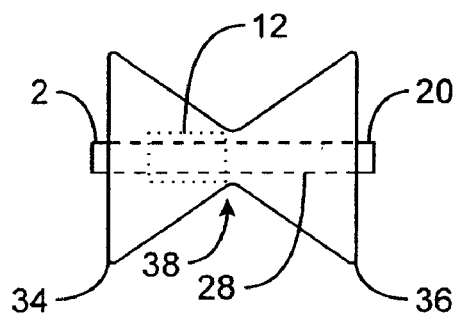
Figure 2D:
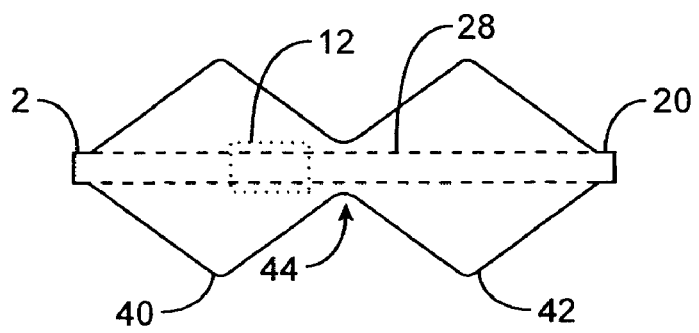

FIG. 2B shows another device variation in which proximal and distal occlusion members 30, 32 may have a cross-sectional shape along a longitudinal axis defined by the device in the form of ellipses, to form ellipsoids. The major axes of the elliptically-shaped occlusion members 30, 32 are preferably oriented perpendicularly relative to the longitudinal axis of the device in this variation, although various angles may be formed as well. FIG. 2C shows the variation in which proximal and distal occlusion members 34, 36 may be formed as triangles, to form conically-shaped occlusion members. In this variation, bridging member 38 may be minimal in length and may simply be formed by the intersection of the occlusion members 34, 38 to form a waist region. FIG. 2D shows yet another variation in which proximal and distal occlusion members 40, 42 may be formed as diamond shapes, to form a variation of conically-shaped occlusion members. This variation may also form a waist region 44.

Although these variations show specific shapes, these are merely intended to be illustrative of the various types of shapes which may be utilized and is not intended to be limiting. For instance, any shape, such as rectangles, squares, etc., which may function to occlude a gastric opening and prevent the device from falling therethrough may be utilized and are within the scope of this disclosure. Moreover, various combinations of the different shapes as occlusion members on a single device may also be utilized, such as a device having a distal occlusion member in the shape of a sphere and a proximal occlusion member in the shape of a cone.

Figure 3A:
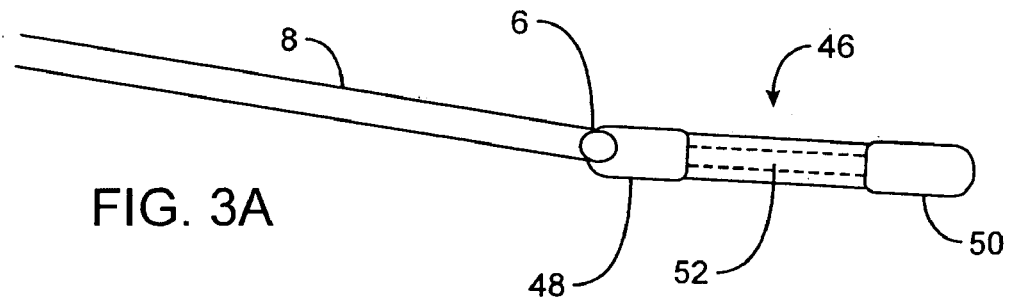
FIGS. 3A to 3C show cross-sectional views of another variation of the pyloric corking device.
Figure 3B:
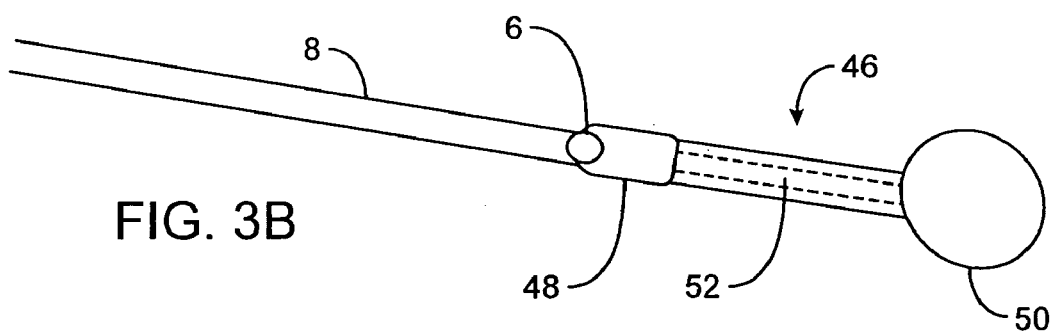
Figure 3C:
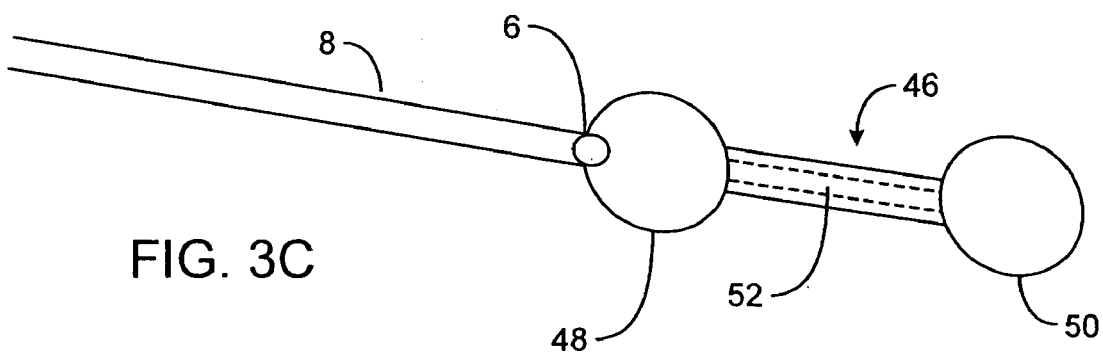

FIGS. 3A to 3C show cross-sectional views of another variation of a pyloric corking device which is also designed to intermittently obstruct a gastric opening. Similar to the device shown in FIGS. 1A to 1C, this particular variation omits the use of a lumen defined through the entire device 46. This device 46 may also incorporate any of the features described above for expanding the occlusion members. For instance, foam of varying expansion pressures may be utilized to ensure that expansion occurs in the distal occlusion member 50 prior to expansion in the proximal occlusion member 48 upon the injection of a fluid, e.g., saline or water, into the device 46. The device 46 is configured so that the influx of fluids from the infusion tubing 8 through the entry port 6 is channeled through the lumen 52 of the central portion from the proximal occlusion member 48 to the distal occlusion member 50. The device 46 may also be placed in the same manner as a device as in FIGS. 1A to 1C, as described in further detail below. This variation may also incorporate an inflation port 6, which may be metallic, so that removal of the device 46, if necessary, can be accomplished through the simple placement of a magnetically tipped suction catheter. The catheter, when appropriately placed, may cause the device to deflate by applying a suction force to facilitate the easy removal of the device 46 from the pyloric valve. The device 46 can thus be removed through any endoscopic or percutaneous approach, e.g., an oro- or nano-gastric approach. While this variation may have a lumen 52 connecting the proximal 48 and distal 50 occlusion members, this lumen 52 may be closed to gastric space and instead be used to communicate an inflation fluid to inflate the occlusion members 48, 50. The occlusion members of the device 46 may have any shape as described above, for instance in FIGS. 1A to 2D.

Figure 4A:
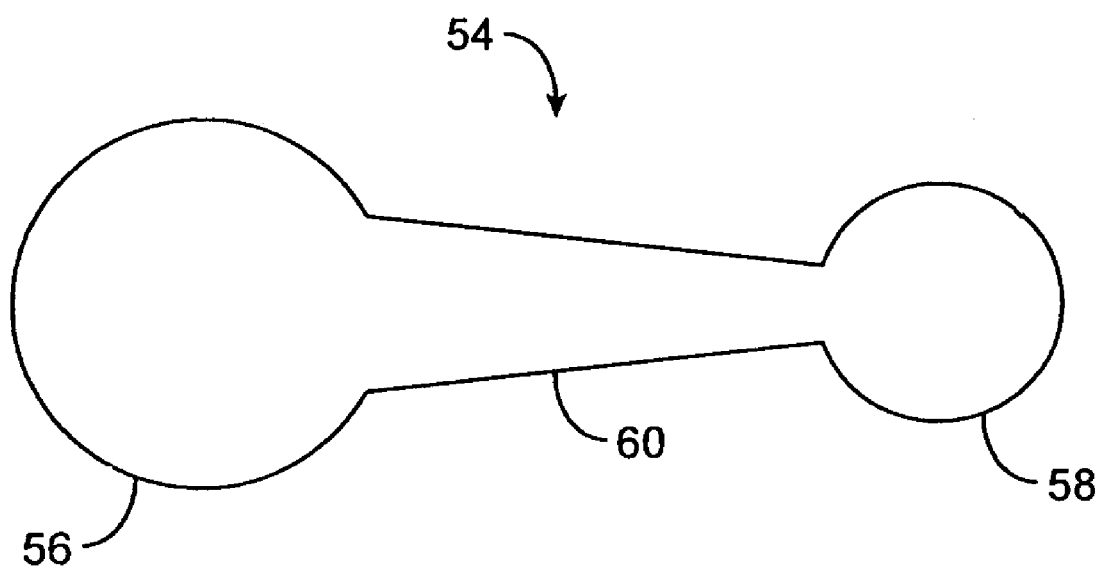
FIG. 4A shows a side view of yet another variation of the device having a tapered bridging member.

Yet another variation of the device is shown in FIG. 4A. In this variation, the device 54 may have a bridging member 60 which is tapered. The bridging member 60 may be tapered to become wider along its length from the distal occlusion member 58 to the proximal occlusion member 56. The tapered bridging member 60 may be utilized to facilitate movement of the device 54 to un-occlude the pyloric valve. As the pyloric valve contracts about the bridging member 60, the taper may aid in moving the device proximally. The angle of the taper may be varied, depending upon the desired results, as may the size and shapes of the occluding members 56, 58.

Figure 4B:
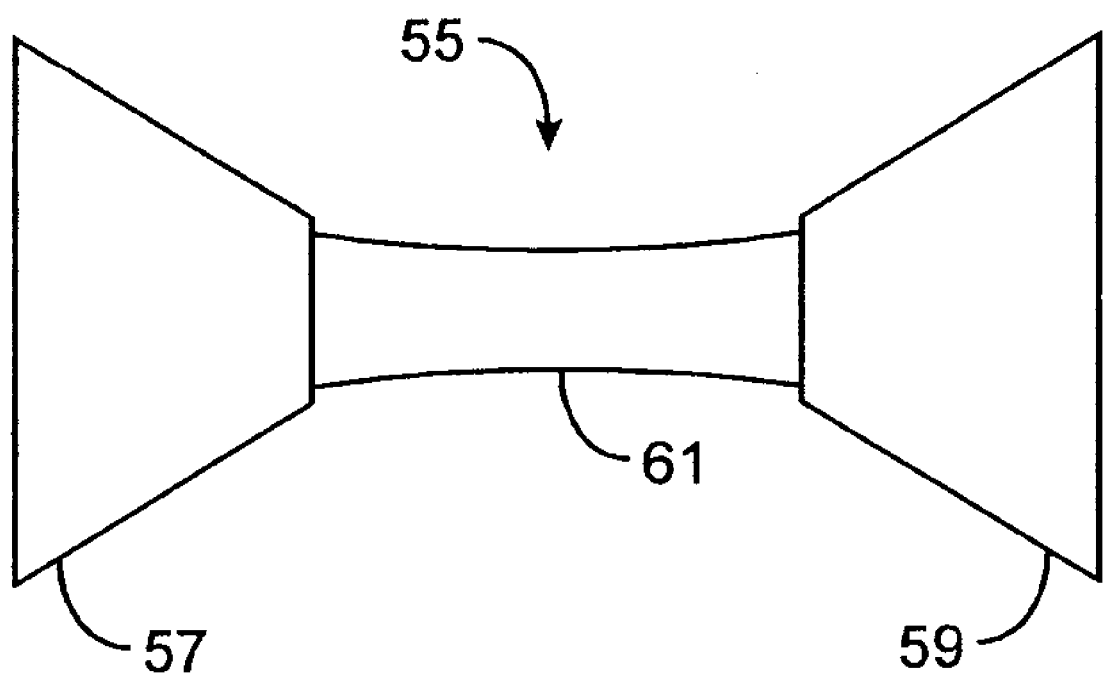
FIG. 4B shows a side view of yet another variation of the device having conical occlusion members held at a distance from one another.

FIG. 4B shows another variation similar to that shown above. In this variation, the device 55 may have occlusion members 57, 59 having conically-shaped members which are connected via a bridging member 61. This bridging member 61 may have a length which holds occlusion members 57, 59 at a distance from one another sufficient to enable the device 55 to move relative to the pyloric valve. The device 55 may inflate or expand the occlusion members 57, 59 using any of the methods disclosed herein and the device 55 may also optionally incorporate a central lumen and a passive or active valve or pumping mechanism, if desired.

Figure 5A:
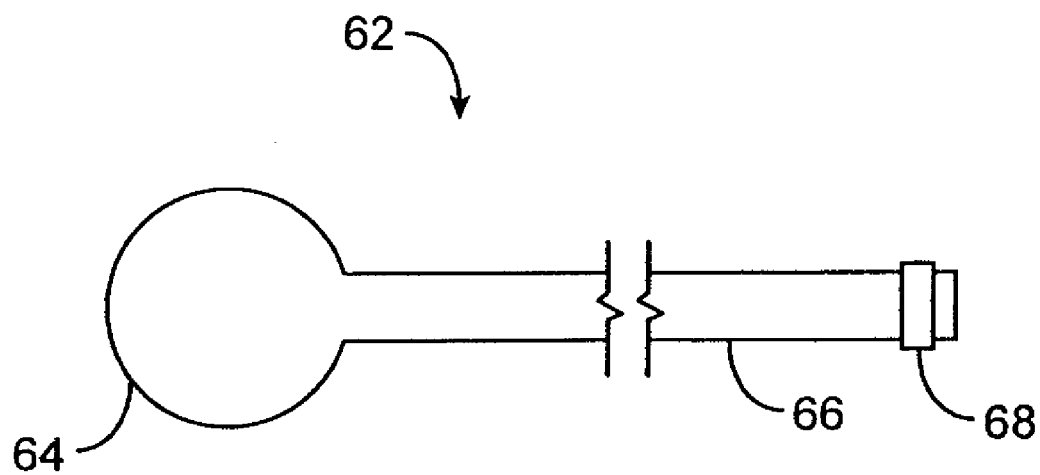
FIGS. 5A and 5B show side views of yet another variation of the device having a single occlusion member and alternative anchor members.
Figure 5B:
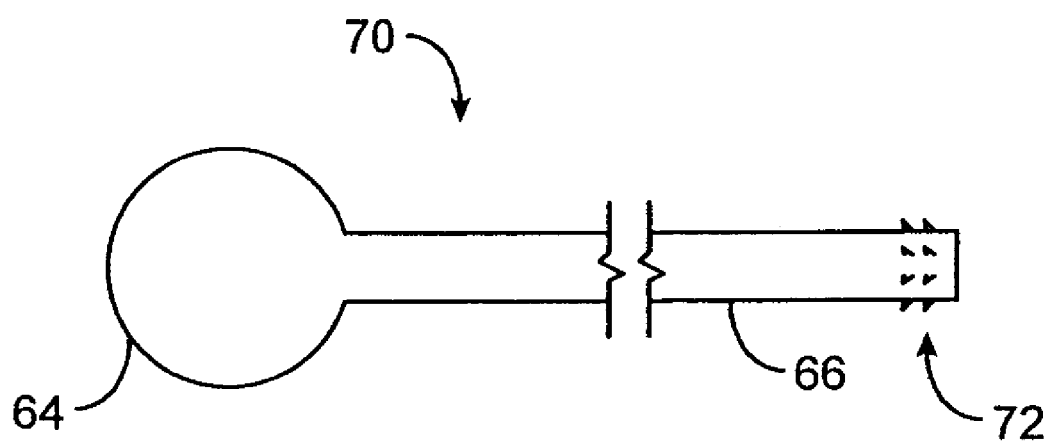

In another embodiment, the distal occlusion member may be omitted entirely. FIG. 5A, for instance, shows a side view of an alternative variation 62 in which the bridging member 66 (or "positioning member") may extend at some length, e.g., 5 cm or greater, from a proximal occlusion member 64. The bridging member 66 may be placed within the intestinal tract, e.g., the duodenum, while held in place by the proximal occlusion member 64 abutting the pyloric valve. The positioning of the proximal occlusion member 64 relative to the pyloric valve may be maintained by the frictional forces generated by the bridging member 66 rubbing against the walls the intestinal tract. The occlusion member 64 may function in the same manner as described above in intermittently un-occluding the pyloric valve during stomach contractions and movement, but may be held in place by the length of the bridging member 66. Although the distal end of the bridging member 68 may be free-floating in the intestinal tract, it may optionally be weighted by a weight 68 or by a number of hooks or barbs 72 for attachment to the intestinal walls, as shown in the device 70 of FIG. 5B.

It is furthermore within the scope of this disclosure that certain features between the different device variations described herein may be incorporated into various combinations. For instance, a device having a proximal occlusion member having a spherical shape and a distal occlusion member having a conical shape may be utilized. As a further example, this device may also incorporate various methods to inflate or expand the distal occlusion member in a different manner as the proximal occlusion member. Moreover, this device may also have a biodegradable covering over only one occlusion member and may also incorporate the valve and/or pump integrated within the device and may also optionally include a lumen defined throughout the length of the device. These examples are merely intended to be illustrative of the various combinations which may be employed by combining various aspects from different variations described herein and are intended to be within the scope of this invention.

Figure 6A:
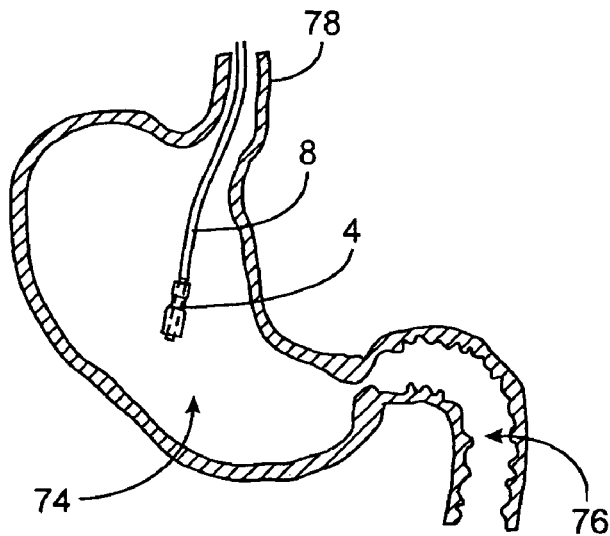
FIGS. 6A to 6C show cross-sectional views of the stomach and one variation for nasogastric (or endoscopic) placement of a non-ingestible variation of the device.
Figure 6B:
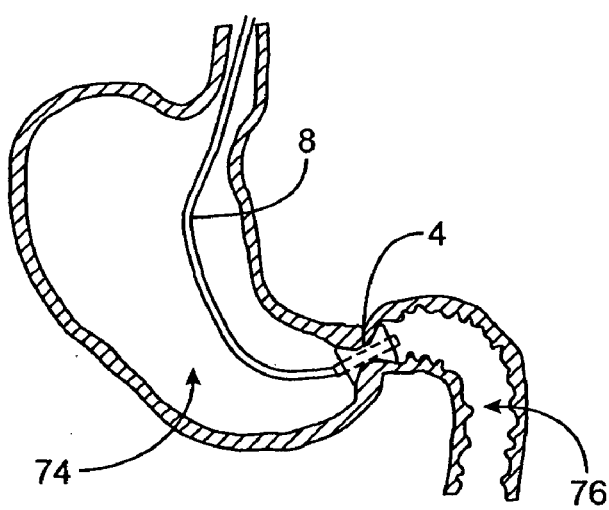
Figure 6C:
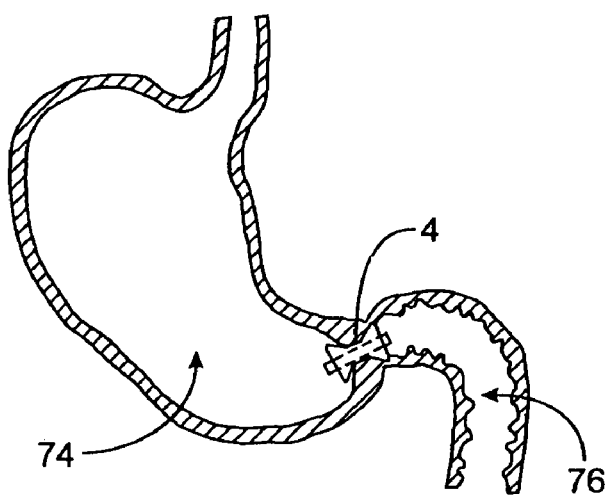

FIGS. 6A to 6C show cross-sectional views of the stomach and one variation for nasogastric (or endoscopic) placement of a non-ingestible, active variation of the device 4. As the device 4 is delivered through the esophagus 78, it may be in a compressed, un-inflated, or un-expanded configuration, as shown in FIG. 6A, while being positioned via the optional tubing 8. Once the device 4 has been positioned to span the pylorus with the occlusion members in the stomach 74 and duodenum 76, respectively, the device 4 may be inflated or expanded using any of the methods described above, as shown in FIG. 6B. The tubing 8 may then be detached and the device 4 left in place, as shown in FIG. 6C.

Figure 7A:
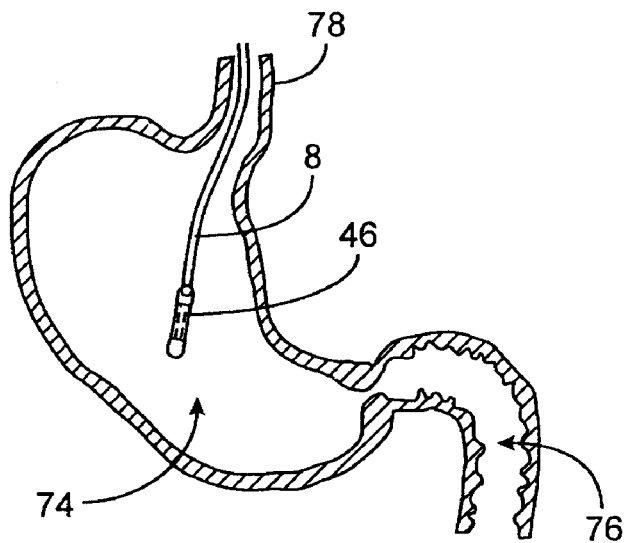
FIGS. 7A to 7C show cross-sectional views of the stomach and another variation for nasogastric (or endoscopic) placement of a non-ingestible variation of the device.
Figure 7B:
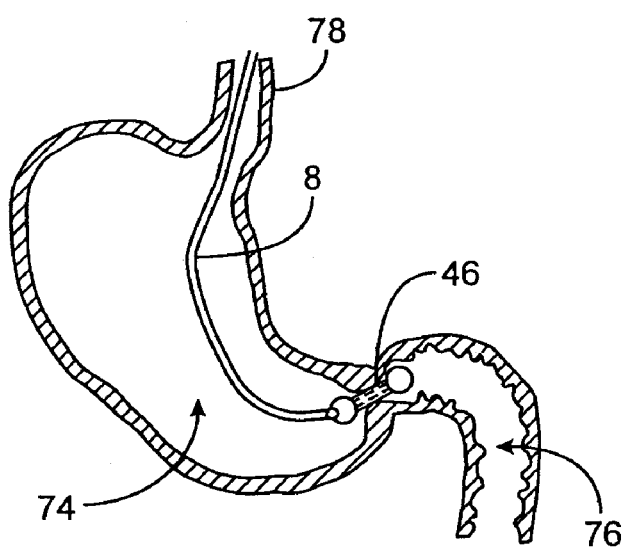
Figure 7C:
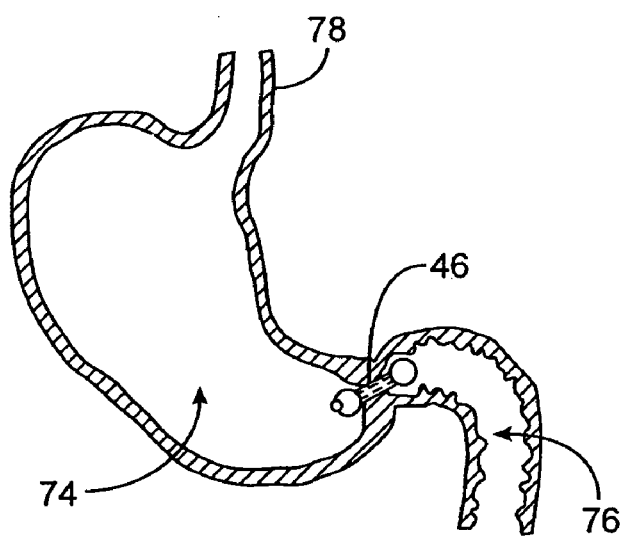

FIGS. 7A to 7C show cross-sectional views of the stomach and another variation for nasogastric (or endoscopic) placement of a non-ingestible, passive variation of the device 46. As above, the device 46 may be advanced through the esophagus 78 while in a compressed, un-inflated, or un-expanded configuration, as shown in FIG. 7A. As shown in FIG. 7B, once the device 46 has been placed spanning the pylorus with the occlusion members in the stomach 74 and duodenum 76, respectively, the device may be inflated or expanded and the tubing 8 may be detached and the device 46 left in place, as shown in FIG. 7C.

Figure 8A:
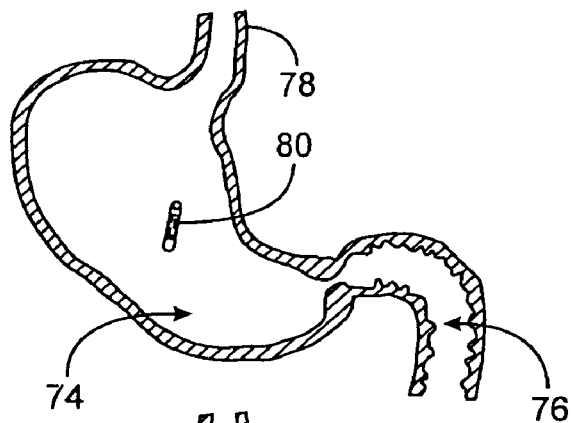
FIGS. 8A to 8D show cross-sectional views of the stomach and yet another variation for placement of a variation of the device through ingestion.
Figure 8B:
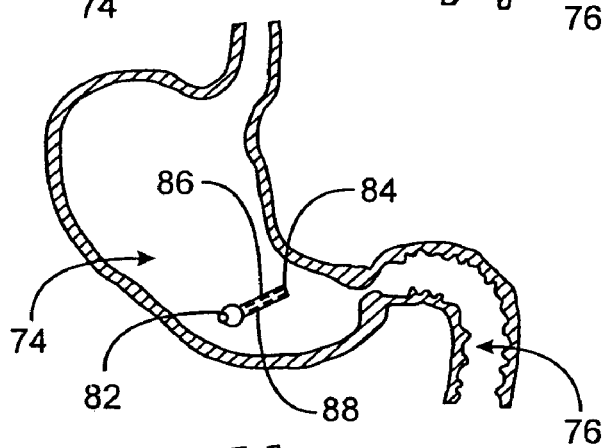
Figure 8C:
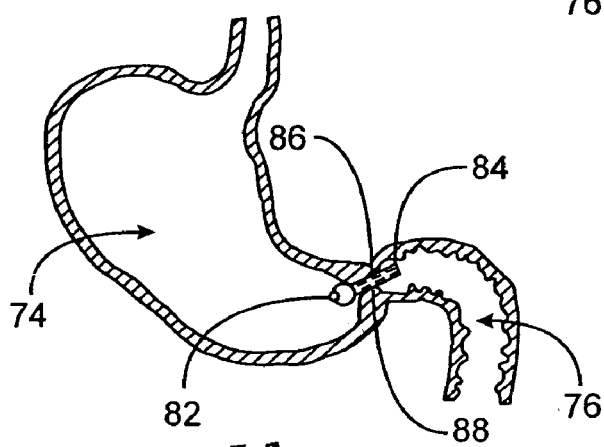
Figure 8D:
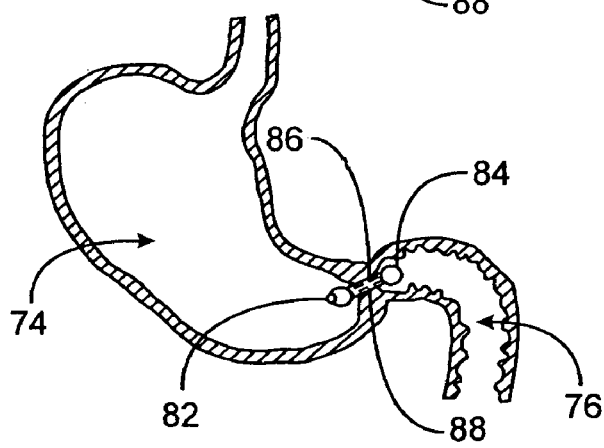

FIGS. 8A to 8D show cross-sectional views of the stomach and yet another variation for placement of a passive (or "self-expanding") embodiment of the device 80. As shown in FIG. 8A, the device 80 may be simply ingested. As it enters the stomach 74, gastric fluids may erode an acid sensitive coating over the inflation port of the proximal occlusion member 82. Once the coating has degraded, the proximal occlusion member 82 may be configured to expand or inflate, as shown in FIG. 8B. Once the expansion or inflation has occurred, the device 80 will remain in the stomach 74 and eventually the distal occlusion member 84 may pass into the duodenum 76 while still in its un-expanded or un-inflated state due to the natural contractions of the stomach, as shown in FIG. 8C. Once the distal occlusion member 84 has passed into the duodenum 76, an alkaline sensitive coating over the distal occlusion member 84 may be eroded and expansion or inflation of the distal occlusion member 84 will occur with the device spanning the pyloric valve, as shown in FIG. 8D. The covering over the distal occlusion member 84 may be configured to erode only once it has contacted the acidic environment specific to the duodenum 76, where the pH level is approximately 6. In order to facilitate removal, the two occlusion members 82, 84 may be connected by a central, hollow lumen 86, as described above, with a barrier 88 designed to rupture upon the application of a predetermined pressure level. Thus, with application of a vacuum having the appropriate pressure level, the barrier 88 may be configured to rupture and the entire device 80 may be deflated.

Figure 9A:
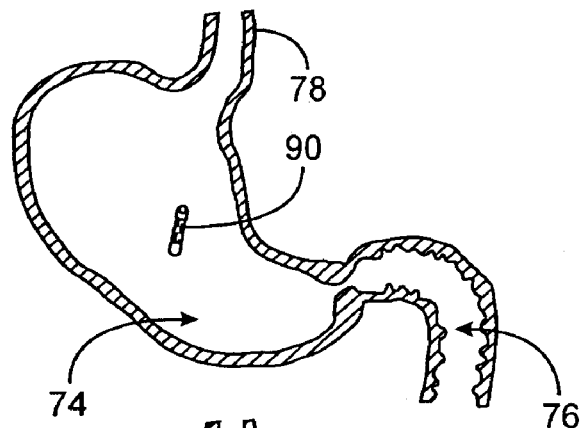
FIGS. 9A to 9D show cross-sectional views of the stomach and yet another variation for placement of another variation of the device through ingestion.
Figure 9B:
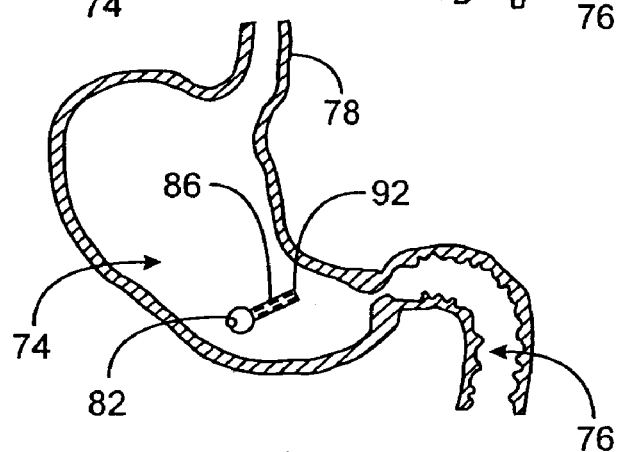
Figure 9C:
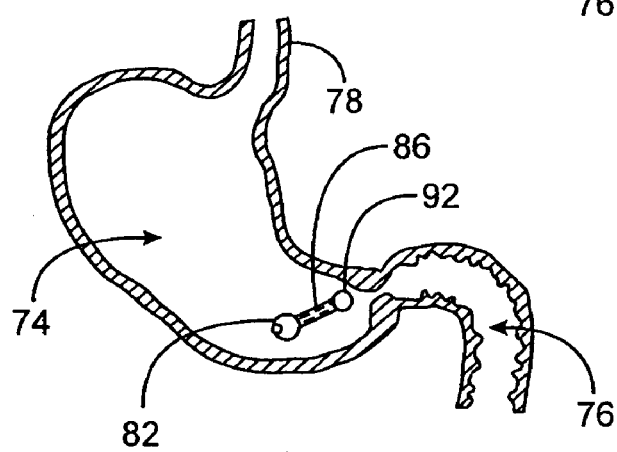
Figure 9D:
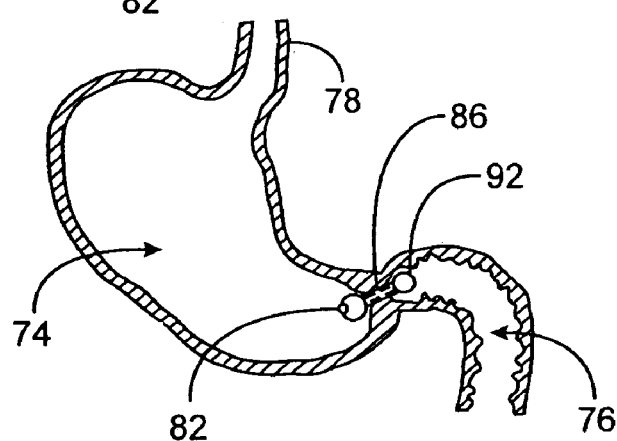

FIGS. 9A to 9D show cross-sectional views of the stomach and yet another variation for placement of a passive variation of the device 90 through ingestion. In this alternative variation, the device 90 can be ingested orally. As the device 90 enters the stomach 74, shown in FIG. 9A, both the proximal and distal occlusion members 82, 92, respectively, may be configured to inflate upon erosion of acid-sensitive coatings over the inflation port or device 90, as shown in FIGS. 9B and 9C. Once inflation or expansion has been accomplished, the distal occlusion member 92 will eventually be passed due to its smaller size (approximately the diameter of the dilated pyloric valve 5-15 mm) while the proximal occlusion member 82 will remain in the stomach 74 due to its larger size, e.g., 15 mm or greater in diameter and up to 60 mm in diameter due to physiologic limitations in the pyloric region of the stomach, as shown in FIG. 9D. Thus, one occlusion member 92 may be designed to be small enough to be passed through the pyloric valve while the proximal occlusion member 82 may be designed to be retained in the stomach 74 with both occlusion members 82, 92 inflating in the stomach 74.

A number of different alternatives and variations may be employed in self-expanding or "passive" pyloric valve obstructing devices and methods such as those just described. In some embodiments, a device may be folded, compressed or otherwise formed into a smaller configuration for swallowing by a patient, without using a biodegradable coating. Upon passing through the esophagus into the stomach, the folded device may unfold due to one or more shape-memory Nitinol support rings or other self-expanding support members. In any swallowing embodiment, a device may also include a tether that extends from the device, back through the esophagus to the patient's mouth. Such a tether may be used for retaining the obstructing device in the stomach until it expands, retrieving the obstructing device if it does not deploy as desired in the patient's stomach and/or the like. In some embodiments, the tether may be swallowed to dissolve in the stomach. In other embodiments, a swallowed device may contact the pyloric valve but not include a bridging member for spanning the valve. Other variations are contemplated within the scope of the invention, according to various embodiments.

Figure 10A:
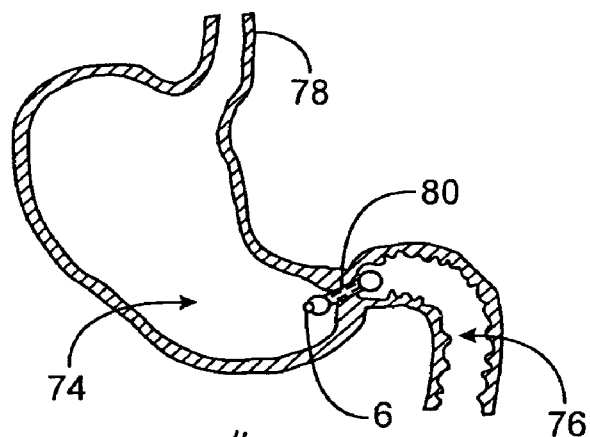
FIGS. 10A to 10D show cross-sectional views of the stomach and one variation for removal of the device.
Figure 10B:
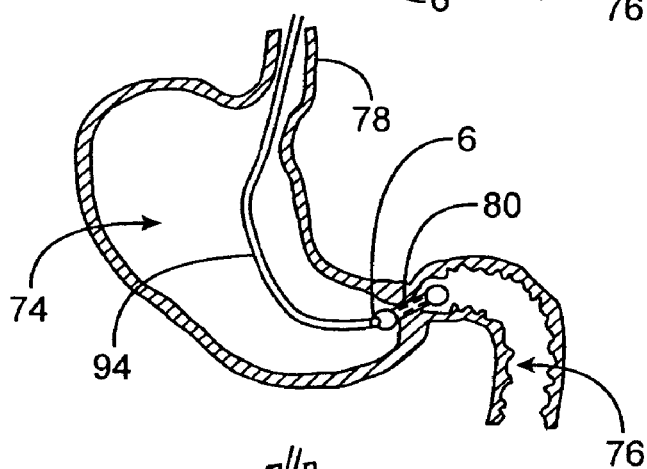
Figure 10C:
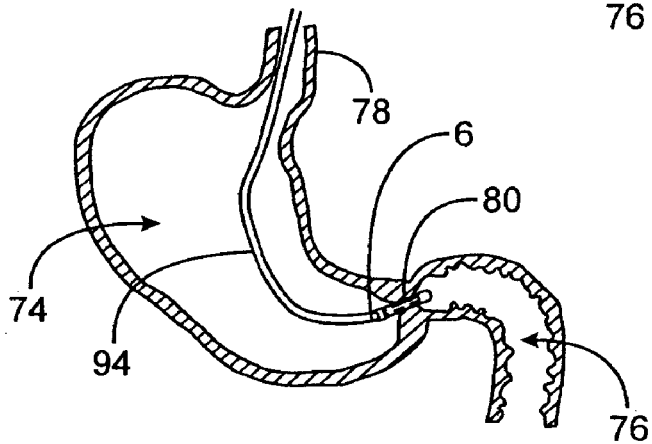
Figure 10D:
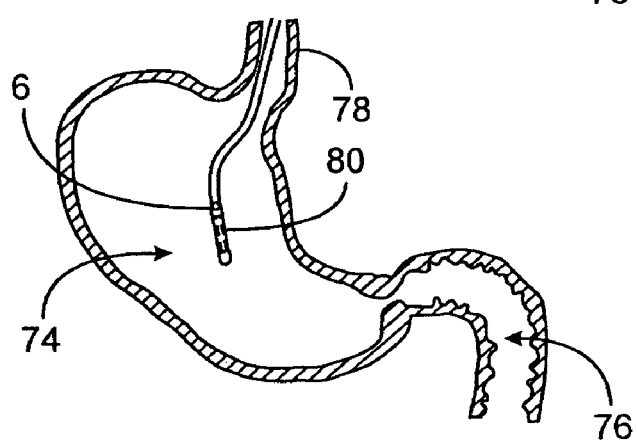

FIGS. 10A to 10D show cross-sectional views of the stomach 74 showing one variation for removal of the device 80 (passive variation illustrated). The device 80 is shown in FIG. 10A between the stomach 74 and the duodenum 76. As seen in FIG. 10B, a magnetic tipped suction catheter or endoscope 94 is introduced and the device 80 may be deflated and removed, as shown in FIGS. 10C and 10D. In contacting the inflation port 6 with the catheter 94, the tip may be configured with an electrical contact as an aid in determining whether the catheter 94 has properly contacted the inflation port 6. Alternatively, the device 80 may be removed through endoscopy or it may be designed to degrade over time and eventually be passed through the intestines.

In other embodiments, an obstruction device may be removed by deflating or collapsing the device and removing it through a lumen of a catheter device. In one embodiment, the device may be cut into small pieces and removed through a catheter lumen. in yet another embodiment, the device may dissolve over time and pass harmlessly through the pyloric valve and the digestive system. Any number of suitable alternatives for removal or passage of the device are possible in various embodiments.

Figure 11A:
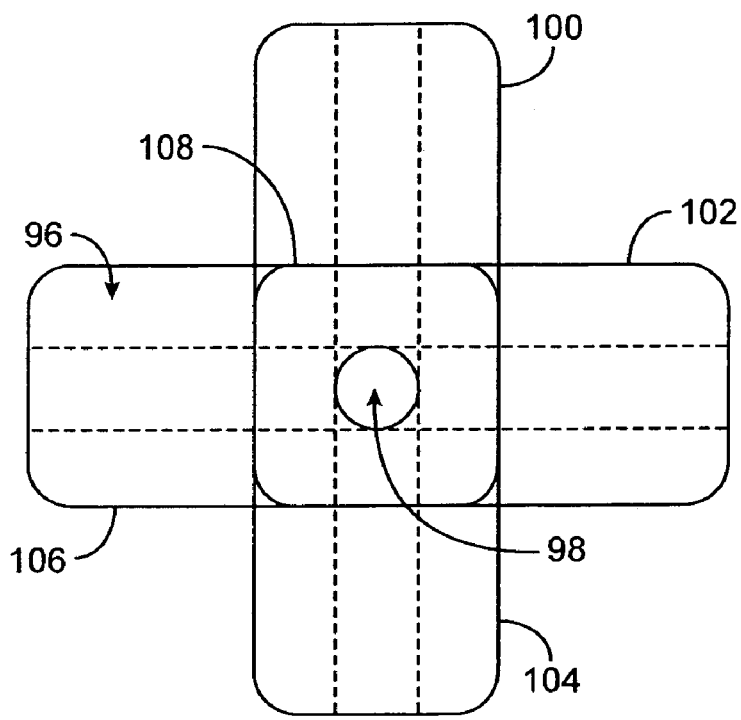
FIGS. 11A and 11B show top and perspective views, respectively, of an alternative variation of the device incorporating multiple prongs designed to intermittently obstruct the pyloric valve.
Figure 11B:
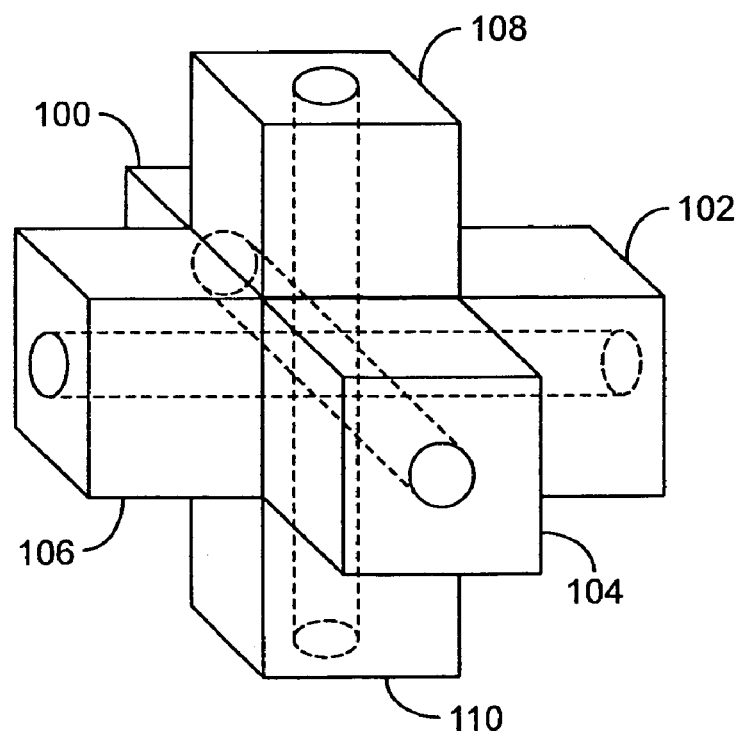

FIGS. 11A and 11B show top and perspective views, respectively, of an alternative variation for the device which may reside solely in the stomach. This particular variation may incorporate multiple prongs 100, 102, 104, 106, 108, 110 designed to intermittently cork the pylorus. In this variation, an expansile material 96 may be appropriately shaped in order to promote occlusion of the pylorus. The device may be ejected from the pylorus due to contractions, but may be re-inserted through one of the various prongs. As a further measure, the device may define multiple apertures 98 through each set of prongs to prevent complete obstruction of the pyloric valve.

Figure 12A:
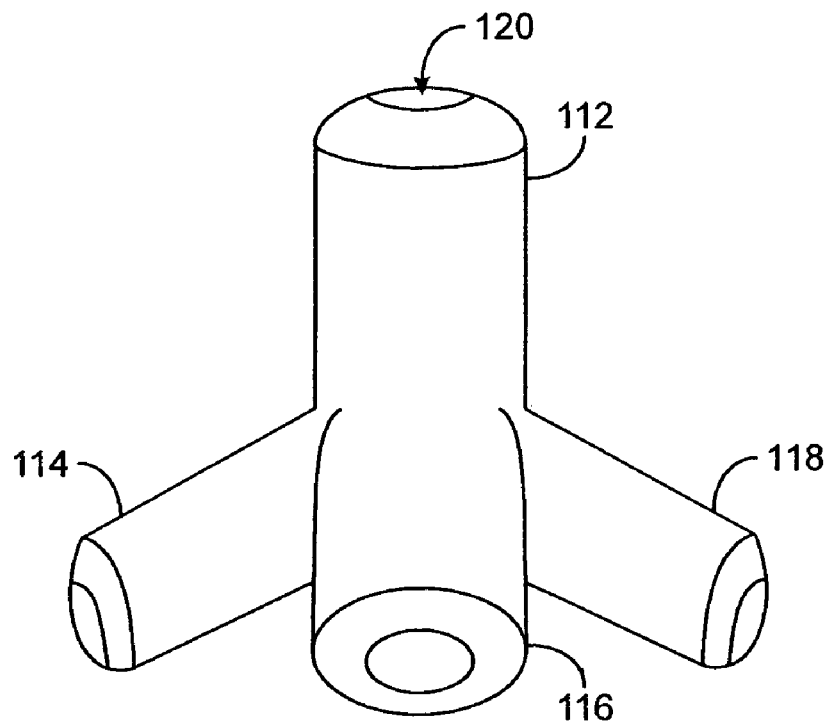
FIGS. 12A and 12B show side and top views, respectively, of another variation of the device incorporating multiple prongs designed to intermittently obstruct the pyloric valve.
Figure 12B:
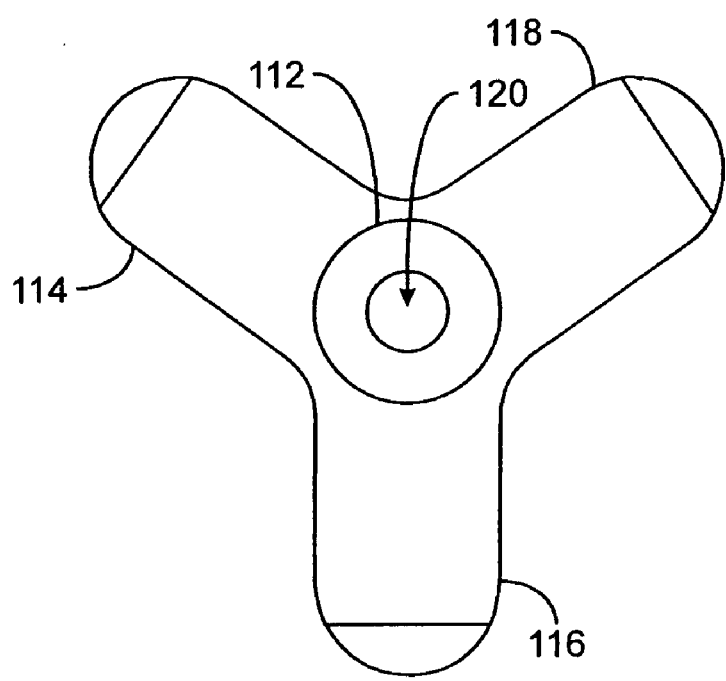
Figure 13A:
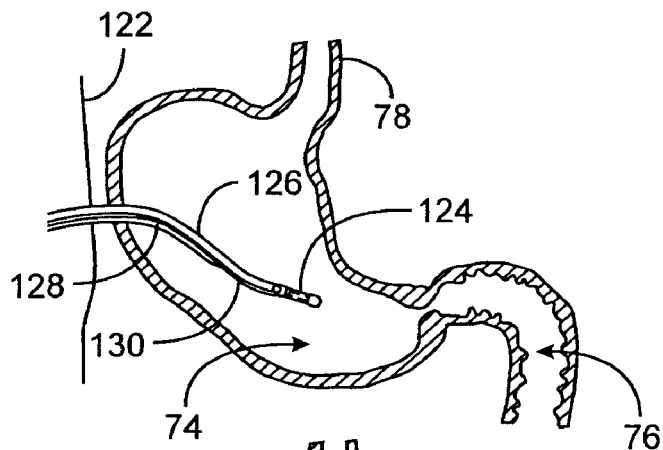
FIGS. 13A to 13D show cross-sectional views of an alternative use of the device for preventing gastroduodenal reflux during tube feeding.
Figure 13B:
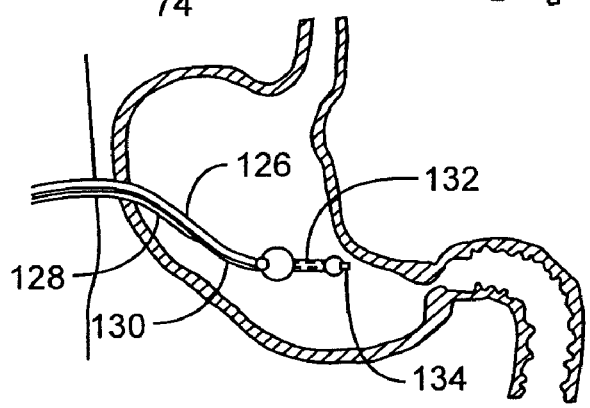
Figure 13C:
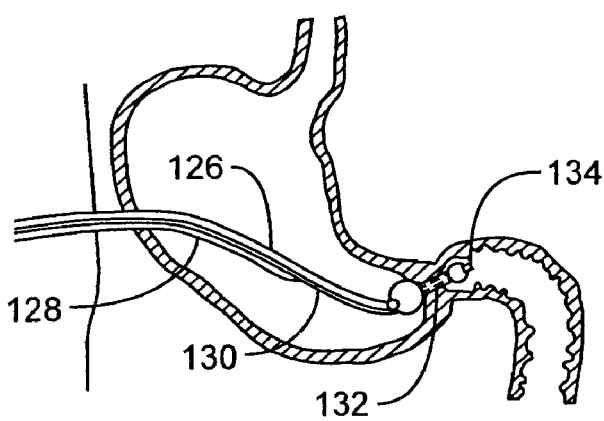
Figure 13D:
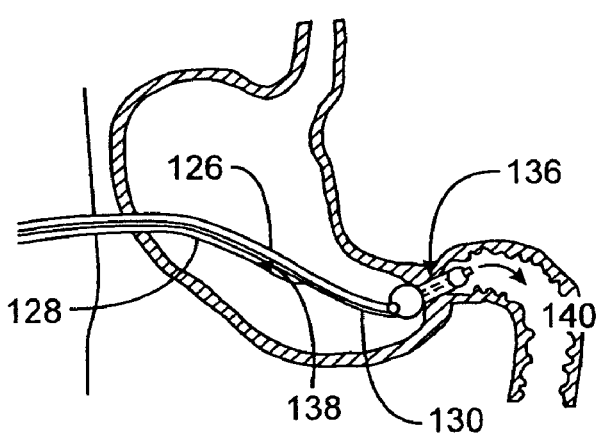

FIGS. 12A and 12B show side and top views, respectively, of another variation of A device as in FIGS. 11A and 11B. In this variation, a fewer number of multiple prongs 112, 114, 116, 118 may be utilized and each prong may also define an aperture 120 therethrough. However, as shown in this variation, each of the prongs may be flexible and tapered or rounded to prevent damage to the surrounding tissue.

FIGS. 13A to 13D show cross-sectional views of an alternative use of the devices described herein. In this variation, the device may be utilized in the prevention of gastroduodenal reflux during tube feeding. As shown, the device 124 is similar to variations described above; however, in this variation, a lumen 132 defined through the device 124 for tube feed delivery may define an outlet 134 designed to be positioned in the duodenum 76. The proximal portion of the device 124 may also be attached to a feeding tube 126 and an inflation tubing 130. Feeding tube 126 may be used to deliver tube feeds through the lumen 132 directly to the duodenum 140 while the inflation tubing 130 may be used to inflate an inflatable pyloric spanner or bridging member 136 during tube feeding to prevent reflux of delivered material 140. The device 124 can also incorporate a third tube 128 which may provide for aspiration of the gastric contents 138 to prevent reflux of the delivered material into the lungs and to decompress the stomach 74. The proximal portion of the occlusive member can either maintain its inflated or expanded state or it can be decompressed at times to relieve pressure on the pyloric valve. In this variation, a percutaneous approach is shown, but a nasogastric approach or another approach is possible.

Figure 14A:
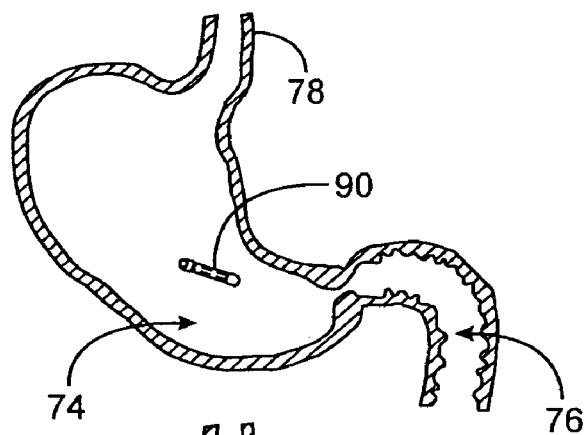
FIGS. 14A to 14D show cross-sectional views of an alternative use of the device in combination with one or several gastric fillers.
Figure 14B:
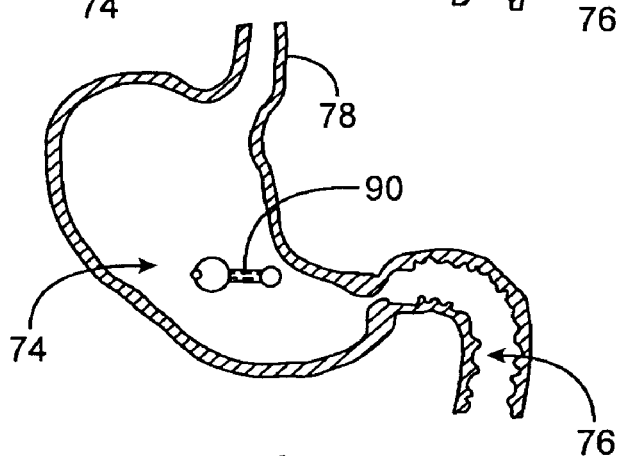
Figure 14C:
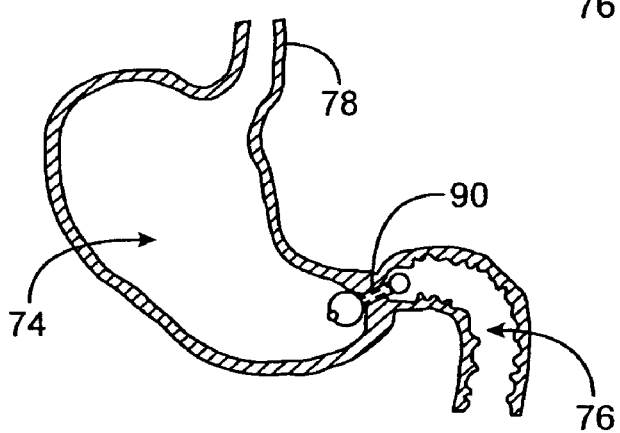
Figure 14D:
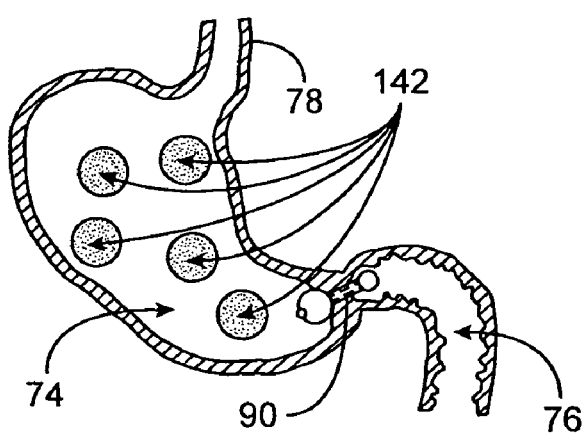

FIGS. 14A to 14D show cross-sectional views of yet another alternative use of devices of the present invention. As shown in FIGS. 14A to 14C, a device 90 may be placed to occlude the pyloric valve. In this case, the device 90 is shown as having been ingested, although placement of the device 90 may be affected via any of the methods described above. As shown in FIG. 14D, the addition of one or several gastric fillers 142, e.g., inflatable gastric balloons, expandable scaffolding, or any other number of space-occupying devices generally known in the art, may be utilized. In this variation, the device 90 may be placed and then the gastric fillers 142 may be introduced. The device 90 may be utilized to ensure that the gastric fillers 142 are not passed through the pyloric valve until they are sufficiently small, thereby allowing for non-degradable substances to be utilized without the concomitant risk of small bowel obstruction.

Figure 15A:
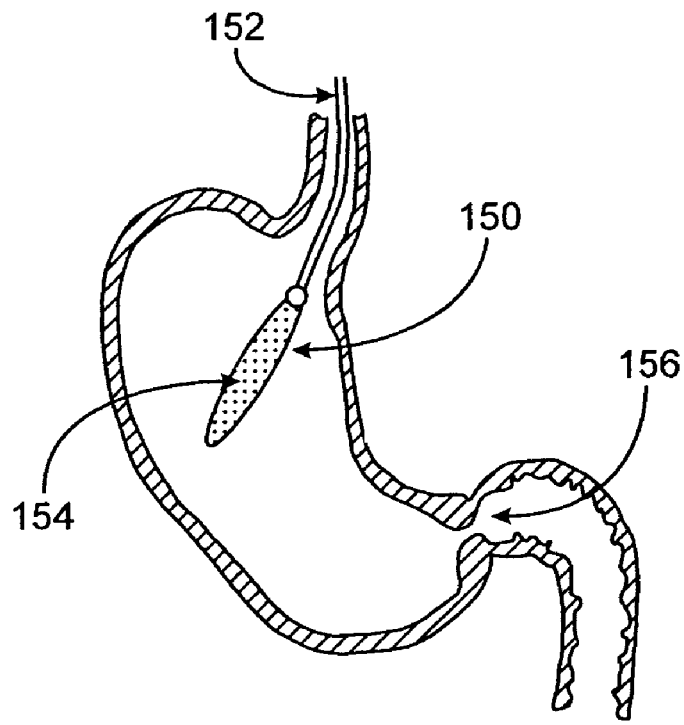
FIGS. 15A to 15D show cross-sectional views of a device designed to partially displace intragastric volume and intermittently obstruct a gastric opening, according to one embodiment of the present invention.
Figure 15B:
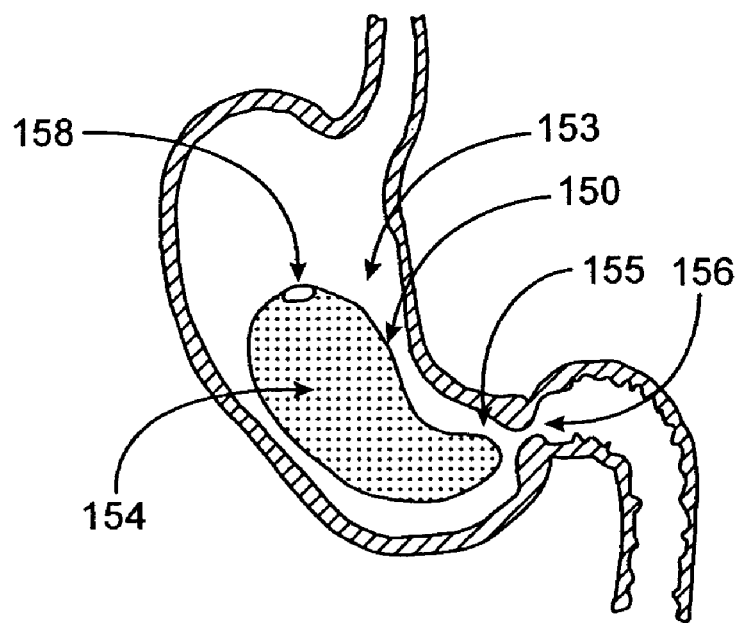

FIGS. 15A to 15D are cross-sectional views demonstrating the use of another embodiment of a device 150 for intermittently obstructing a pyloric valve 156, and in this embodiment for partially filling the gastric space. FIG. 15A illustrates the device 150 in an unexpanded or uninflated state and ready for delivery and/or insertion into the stomach via a catheter device 152, such as an endoscope, tubing or the like. The device, in this embodiment, includes an expandable foam 154, which is expanded when the device 150 is within the stomach, as shown in FIG. 15B. Any suitable nontoxic liquids or gases may be introduced through an inflation port 158, for expanding the device 150 and/or the foam 154.

Any suitable materials may be used to form the device 150. In one embodiment, for example, the device 150 may comprise an expandable balloon fabricated from silicone, silicone elastomers, latex, polyurethane, PTFE, FEP, and/or the like. Alternatively, self-expanding materials, such as foam or hydrogels which typically expand upon contact with fluids, may be utilized within the device 150. If such self-expanding materials are utilized, they may be disposed in the device 150, and a fluid such as saline may be infused to expand the materials.

As shown in FIG. 15B, the device 150 in one embodiment includes a proximal portion 153 and a distal portion 155. In some embodiments, the proximal portion 153 has a supportive or structural function, for assuring that the device 150 has a large enough cross sectional diameter to prevent passage of the device 150 through the pyloric valve. Typically, the distal portion 155 functions to contact the pyloric valve 156 and/or tissue adjacent the pyloric valve 156, to intermittently and/or partially block the valve 156. In some embodiments, the distal portion 155 is made of compliant material, so that when it contacts stomach tissue in, around or adjacent the pyloric valve 156, it does not harm the tissue. In some embodiments the proximal portion 153 and distal portion 155 are made of the same material, with the proximal portion 153 having a greater amount of material, greater wall thickness or the like, relative to the distal portion 155.

Generally, the device 150 may have any of a number of suitable shapes, such as an irregular oblong shape as shown, an elongated spherical shape, a cone, a diamond or the like. In some embodiments, the shape is selected such that the device 150 naturally migrates toward the pyloric valve 156, with the distal portion 155 aligned to contact the valve 156. In these and other embodiments, migration of the device 150 to the valve 156 may be further enhanced by selecting a specific gravity or buoyancy of the device to allow it to move through the stomach contents towards the valve 156.

Figure 15C:
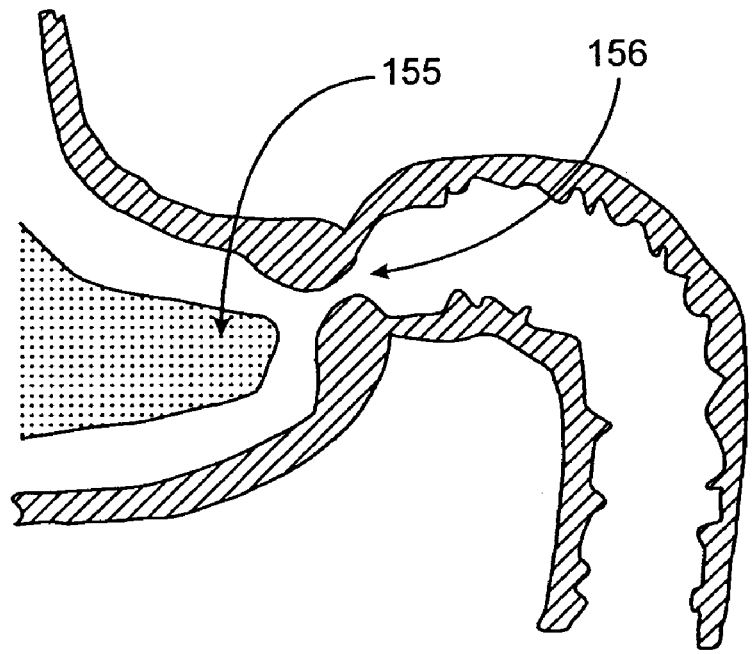
Figure 15D:
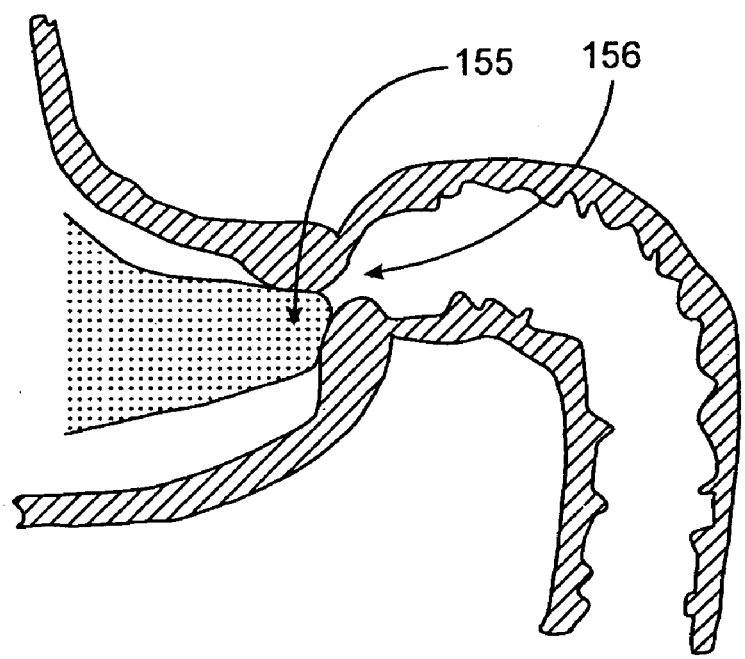

FIGS. 15C and 15D the distal portion 155 of the device 150 in interacting with the pyloric valve 156. As illustrated, the shape of the distal portion 155 is configured to move out of (FIG. 15C) and into (FIG. 15D) contact with the valve 156. This typically occurs during the natural contractions of the stomach, thus providing for intermittent obstruction of the pyloric valve 156. Intermittent obstruction of the pyloric valve 156 causes food in the stomach to be retained longer, and thus, feelings of satiation may be initiated sooner and may last longer, leading the patient to consume less food. In the embodiment shown in FIGS. 15C and 15D, the distal portion 155 fully obstructs the valve 156 when it is in contact. In alternative embodiments, the distal portion 155 may not fully obstruct the valve 156 and may have any of a number of various configurations designed to allow partial flow even when fully contacting the pyloric valve 156. For example, the distal portion 155 may have a shape such as conical, ellipsoid, spherical, pyramidal, tubular, disc-shaped with a protruding member (designed to fit within the pylorus) or the like. In one embodiment, the distal portion 155 and the proximal portion 153 have identical or nearly identical shapes, so that either end may obstruct the pyloric valve 156, regardless of the orientation of the device 150.

The device 150 may have any of a number of additional features for enhancing its delivery into the stomach, it ability to intermittently obstruct the pyloric valve 156, its removal from the stomach and/or the like. In one embodiment, for example, the device 150 includes one or more radiopaque markers, dyes and/or materials for facilitating visualization of the device 150. The device 150 may also include other markers, dyes or materials that enhance its visibility to the naked eye, which may be advantageous in embodiments where the device 150 dissolves and passes through the body or as a safety feature in the unlikely event that the device 150 breaks or ruptures.

In some embodiments, the device 150 may include one or more mechanisms for releasing one or more drugs into the stomach or small intestine beyond the pyloric valve. For example, slow-releasing drugs may be coupled with or infused into materials covering the device 150 or materials used to construct the device 150. These drugs, which may be any of a number of therapeutic or diagnostic agents, may slowly infuse into the patient by drug release into the intestinal tract or through contact with the patient. In other embodiments, the device 150 may incorporate electrical stimulation technologies. For instance, electrical probes may extend from a surface of the device 150 for insertion into the surrounding tissue or electrodes may be formed over a surface of the device 150.

In one embodiment, the device 150 may be covered by an erodable or biodegradable covering for delivery into the stomach. Such a covering may be configured to constrain the device 150, and once the covering comes into contact with substances in the gastric lumen, it may naturally break down and dissolve, thus releasing the device 150 and allowing it to expand. In one embodiment, the device 150 may be covered by different materials each configured to erode at differing rates or in different chemical environments within the stomach.

Figure 16:
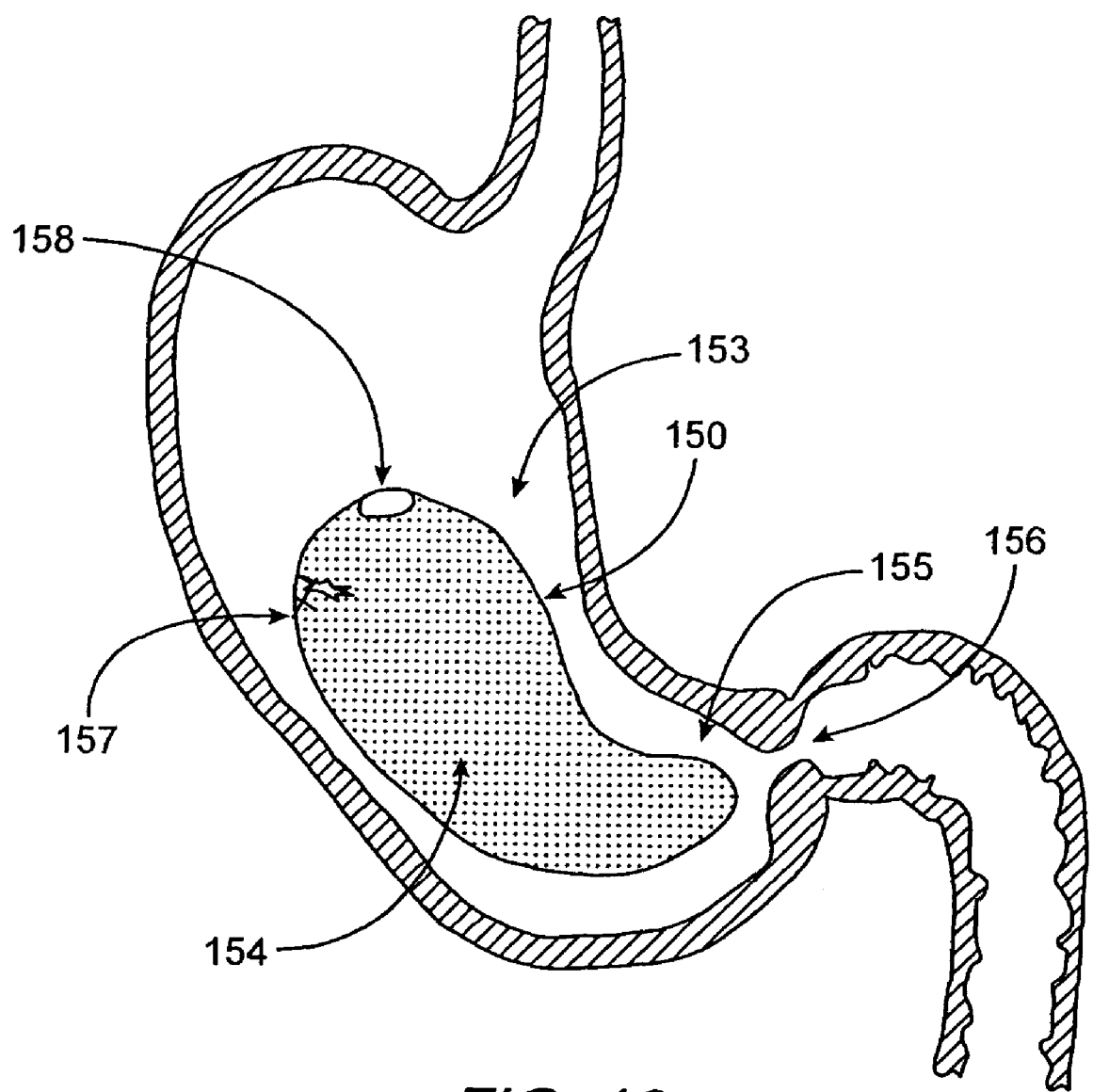
FIG. 16 shows a cross-sectional view of a device as in FIGS. 15A to 15D with a rupture.

FIG. 16 illustrates the device 150 of FIGS. 15A to 15D, in which a rupture 157 has occurred. As demonstrated by this figure, the overall shape of the device 150 is maintained due to expanded foam 154 (or other framework material or the like within or on the device 150 in other embodiments). Generally, the foam or framework material will be acid-resistant in order to prevent its degradation within the stomach and thus allow it to support the device 150 for extended periods of time after rupture has occurred. In an alternative embodiment, the foam 154 or other framework material may degrade slowly after rupture while releasing a signaling material that would alert the patient to the rupture upon examination of feces. The patient would then know to consult his physician to have the device 150 removed.

Figure 17A:
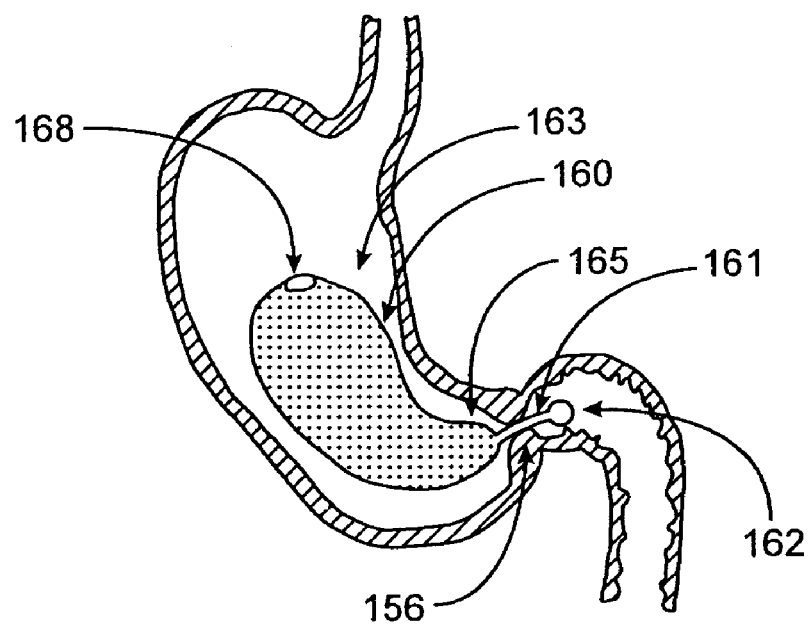
FIG. 17A shows a cross-sectional view of a device having a positioning member and a retaining member, according to one embodiment of the invention.
Figure 17B:
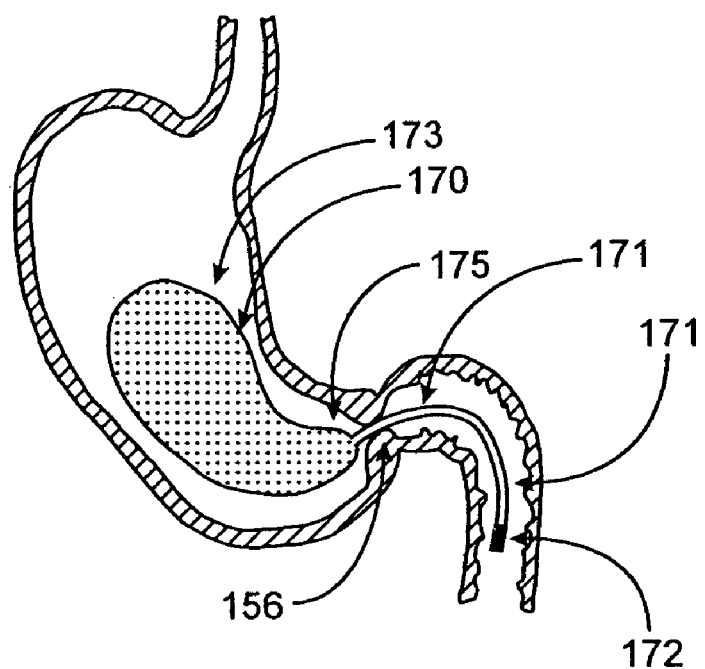
FIG. 17B shows a cross-sectional view of a device having a positioning member with an inflation port, according to one embodiment of the invention.

Referring now to FIGS. 17A and 17B, another embodiment of a pyloric valve obstructing device 160 may include and inflation port 168, a proximal portion 163, a distal portion 165, a positioning member 161 and a retaining member 162. Inflation port 168 is optional, of course, since some embodiments require inflation while others do not. Positioning member 161 generally helps position the device 160 in a location for intermittently obstructing the pyloric valve 156. Retaining member 162 helps maintain the location or position of the device 160.

In one embodiment, the positioning member 161 may be hollow, thus allowing for passage of fluids and/or gases through the device to allow the proximal portion 163, distal portion 165 and retaining member 162 to be inflated. In one embodiment, positioning member 161 may be relatively short, to inhibit movement of the distal portion 165 relative to the pylorus 156. In other embodiments, the positioning member 161 may be longer to allow for more movement of the device 160.

Referring now to FIG. 17B, in another embodiment a device 170 having proximal 173 and distal 175 portions is coupled with a positioning member 171 that includes an inflation port 172 at its distal end. In this embodiment, the device 170 is passed to the stomach in its uninflated state, the positioning member 171 and port 172 are used to inflate the device 170, and the positioning member is then swallowed and passes through the pyloric valve 156 to remain harmlessly in the first part of the small intestine. In another embodiment, the device may be placed into the stomach while attached to a removable tether that extends up the esophagus and into the mouth. The tether can be used to remove the device if it does not properly deploy, or alternatively it can be detached from the device once it is in place in the stomach.

Figure 18A:
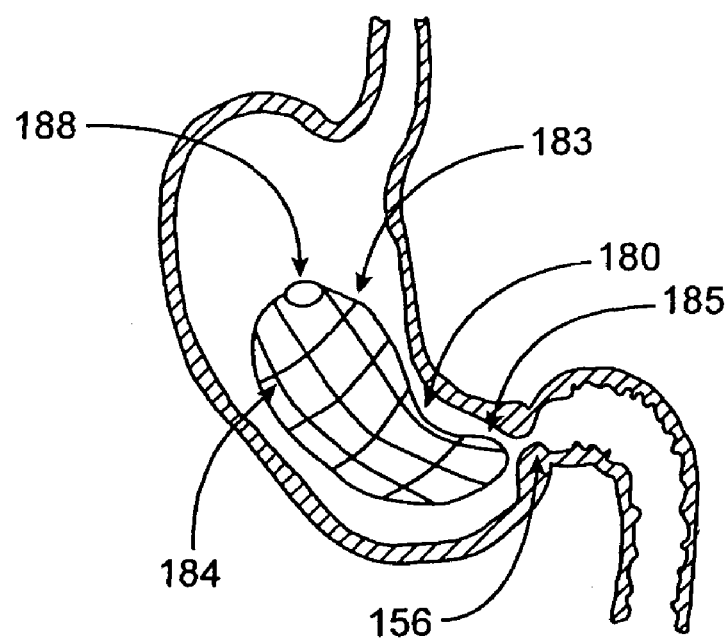
FIGS. 18A and 18B show cross-sectional views of two different embodiments of a device for obstructing a pyloric valve, according to two embodiments.
Figure 18B:
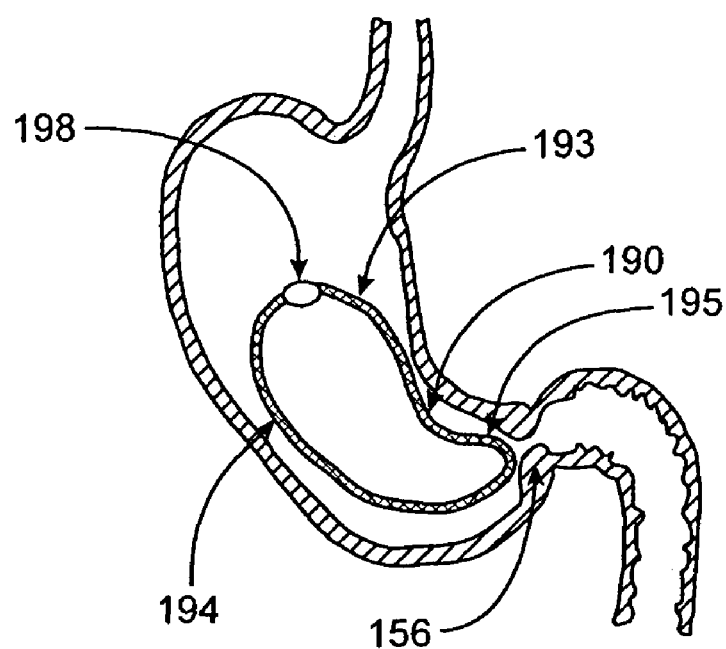

As illustrated in FIGS. 18A and 18B, and as mentioned earlier, various embodiments of a device for obstructing a pyloric valve may include any of a number of different expandable support mechanisms. The embodiments just described included foam, but other supportive structures and materials may be used, such as self-expanding cages, coils, lattices, frameworks or the like. In FIG. 18A, a device 180 having proximal 183 and distal 185 portions as well as an inflation port 188 also includes an expanding scaffolding 184, which may be coupled with the wall of the device 180 on its inner surface or outer surface, or which may be embedded in the wall. Such an expanding scaffolding 184 may be composed of shape memory or super-elastic materials, such as Nitinol. The scaffold 184 may be compressed into a delivery configuration and then either allowed to expand into the desired occlusive shape by self-expansion or expanded by supplying an activation energy, such as, electrical energy, heat, RF energy or the like. In another embodiment, the scaffold may be deployed by pulling the scaffold into an expanded configuration with a pulling device, and in such embodiments the scaffold may have a catch mechanism to prevent it from collapsing to its original shape.

In the embodiment shown in FIG. 18B, a device 190 includes a proximal portion 193, a distal portion 195 and an inflation port 198. In this embodiment, a wall 194 of the device 190 is made of a shape memory, super-elastic or otherwise self-expanding material, which expands from a smaller configuration to a larger configuration upon release from constraint. The material of the wall 194 then retains its expanded shape, thus maintaining the shape of the device 190 and preventing the device from collapsing.

Figure 19B:
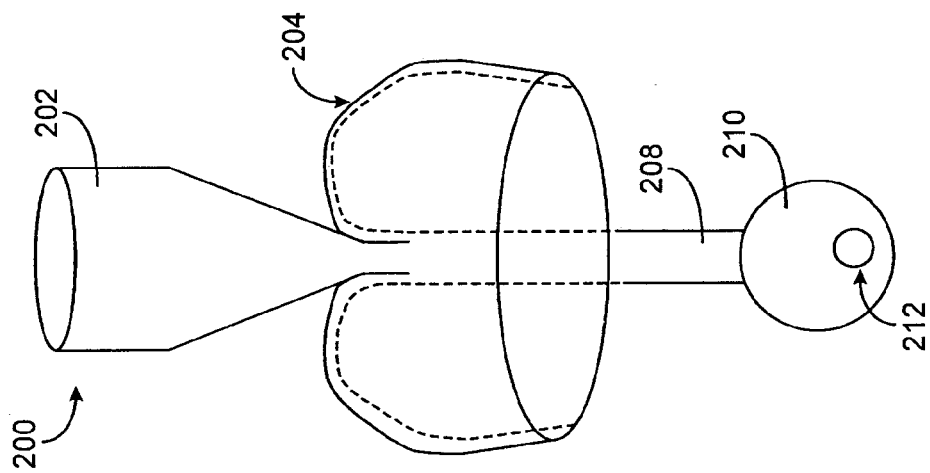
FIGS. 19A and 19B show side views of an device for obstructing a pyloric valve, according to another embodiment.
Figure 19A:
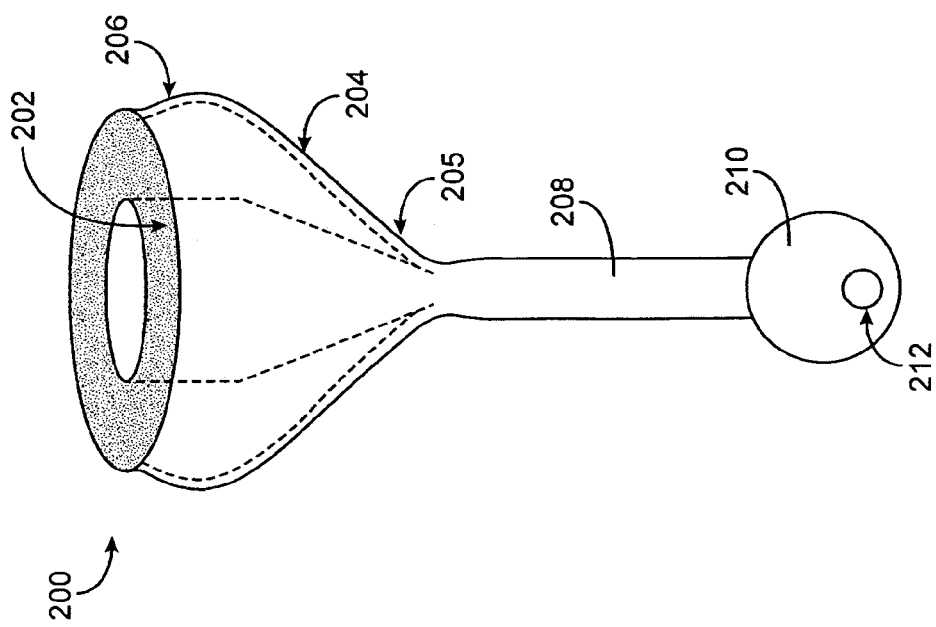

Referring to FIGS. 19A and 19B, another embodiment of a pyloric valve obstructing device 200 includes a movable or "inverted" outer shell 204, an inner core 202, a positioning member 208 and a distal retaining member 210 having a hole 212 or other surface feature. The device 200 is shown in its expanded configuration in FIG. 19A, for intermittently obstructing a pyloric valve, and in its collapsed configuration in FIG. 19B, for delivery into the stomach. The shell 204 includes a tissue contacting/engaging portion 205 and a support portion 206. Generally, the support portion 206 is more rigid/stiffer than the tissue contact portion 205, so that the former helps maintain the cross-sectional diameter of the device 200 so that it cannot pass through the pylorus, while the latter is more compliant so that it can contact stomach tissue without causing significant damage.

The various components of the device 200 may be constructed of any suitable materials, such as those already described or any other suitable materials now known or hereafter discovered. In one embodiment, the inner core 202 is a solid material, such as silicone, but in other embodiments the core 202 may be hollow. The core 202 may have any suitable size, shape, cross-sectional diameter or the like. In one embodiment, the core 202 has a cross-sectional diameter of between about 5 mm and about 30 mm, and preferably about 10 mm. The shell 204 may be made of the same or different material as the core 202, and also may have any suitable size, shape, cross-sectional diameter or the like. In one embodiment, the support portion 206 of the shell 204 is thicker that the tissue contact portion 205. In other embodiments, the support portion 206 may be made of a different material than the tissue contact portion 205.

The positioning member 208 may be an extension of inner core 202, shell 204 or both, or may instead be a separate piece coupled with the inner core 202 and/or outer shell 204. Positioning member 208 may have any suitable length and diameter to allow it to pass through the pyloric valve. In one embodiment its cross-sectional diameter is about 1.0 cm or less and its length is about 3.0 cm or greater. The retaining member 210 may also have any suitable size, shape or configuration, with some embodiments being expandable, some being self-expanding, and others configured to not expand at all. In one embodiment, the retaining member 210 has a greatest cross-sectional diameter of about 30 mm or smaller, and preferably about 25 mm or smaller, and even more preferable about 21 mm or smaller. The hole 212 or surface feature in the retaining member 210 may have any configuration for allowing coupling of an actuator or other device with the retaining member for delivering, adjusting and/or retrieving the device 200. Both the positioning member 208 and the retaining member 210 may be made of any suitable material.

Although not drawn to scale, FIG. 19B illustrates the collapsed or inverted state of the device 200. In this configuration, the shell 204 may be compressed to a smaller cross-sectional diameter for delivery, such as through a delivery tube or catheter. After the device 200 is delivered to the stomach, the shell 204 is inverted to its expanded state and the device 200 may then act to intermittently obstruct the pyloric valve.

FIGS. 20A to 20C illustrate a method for delivering and deploying the device 200 of FIGS. 19A and 19B in a stomach. In FIG. 20A, the device 200 is housed within the lumen of a delivery tube 214 or catheter in its collapsed configuration. In FIG. 20B, the device has been advanced partially out of the delivery tube, allowing the shell 204 to at least partially expand. An actuator 216 hooked through the hole 212 on the retaining member 210 may then be used to pull back on the device 200, such that the shell 204 overlaps the distal end of the delivery tube 214. The distal end of the delivery tube 204 is then used to apply force to the shell 204, causing it to invert into its expanded state, as shown in FIG. 20C. As also shown in FIG. 20C, the actuator 216 may include a hook 218 for coupling with the hole 212 in the retaining member 210. Once the shell 204 is moved to its expanded configuration, it is designed to stay in that configuration, thus providing the pyloric valve contacting and device retention functions described above. In one embodiment, the delivery tube 214 may include an expandable balloon (not shown) at or near its distal end. The balloon maybe doughnut-shaped to inflate circumferentially, or may be have an eccentric shape or any other suitable shape. The balloon may be inflated and serve as a stop against which the device 200 may be pulled. Alternatively, the balloon may be inflated under or within the device 200 to invert the device 200 as the balloon inflates.

In other embodiments, the device may be delivered and/or deployed using any other suitable method. For example, in one embodiment the shell 204 may "self-invert" from its constrained/collapsed state to its expanded state without using an actuator 216 or the distal end of a delivery device 214. Self-inverting may be achieved by shape-memory or spring loaded materials or the like, or by a shell geometry that creates a bias in the stiffness of the device. In another embodiment, the device 200 may be swallowed, either in a folded or otherwise collapsed state or housed within a dissolving caplet. A number of different alternative embodiments are possible.

Although the above is a complete and accurate description of the invention, any of a number of variations, additions and the like may be made to the embodiments described without departing from the scope of the invention. For example, devices and methods described above are not limited strictly to treatment of obesity, but may also be used to treat other conditions. Furthermore, other devices, such as imaging devices, chemical detection devices, space occupying devices and/or the like may be incorporated into many of the embodiments described above without departing from the scope of the invention. Therefore, the foregoing description is provided primarily for exemplary purposes and should not be interpreted to limit the scope of the invention as it is defined in the following claims.

We claim:

1. A device for obstructing a pyloric valve of a stomach, the device comprising:
   an expandable support portion adapted to reconfigure in the stomach from a first configuration to a larger second configuration, wherein the support portion in the second configuration is sized to prevent passage of the device through the pyloric valve;
   a compliant tissue engagement surface comprising a compliant outer shell which is formed external to the expandable support portion when in the larger second configuration such that the surface surrounds an inner plug within a hollow portion formed within the support portion and wherein the surface is adapted to be intermittently engaged to stomach tissue adjacent the pyloric valve whereby the pyloric valve is intermittently obstructed;
   a tubular positioning member having a length extending from the tissue engagement surface and having a shape adapted to pass at least partially through the pyloric valve to position the device over the pyloric valve, where the outer shell is movable from a first configuration in which it overlaps at least part of the positioning member to a second configuration in which it overlaps at least part of the plug; and
   a retaining member having a diameter larger than the positioning member and coupled with a distal end of the positioning member for maintaining the device in intermittent contact with the pyloric valve, where the retaining member has an atraumatic shape.

2. A device as in claim 1, wherein the expandable support portion comprises at least one self-expanding material.

3. A device as in claim 2, wherein the at least one self-expanding material is selected from the group consisting of spring stainless steel, shape-memory materials, super-elastic materials and spring-loaded materials.

4. A device as in claim 2, wherein the self-expanding material comprises a self-expanding foam disposed within at least one of the expandable support portion and the tissue engagement surface.

5. A device as in claim 4, wherein the foam comprises at least one of polyethylene foam, polyurethane foam and silicone foam.

6. A device as in claim 2, wherein the self-expanding material expands upon contacting one or more substances present in the stomach.

7. A device as in claim 1, wherein the tissue engagement surface is adapted to temporarily form a seal with the pyloric valve upon contacting the tissue adjacent the valve, and wherein the tissue engagement portion is sufficiently compliant to avoid causing damage to the tissue on contacting it.

8. A device as in claim 1, wherein the support portion in the second configuration has a widest cross-sectional diameter of between 2.5 cm and 15 cm.

9. A device as in claim 1, wherein the support portion and the tissue engagement portion have a combined volume in the second configuration greater than 200 cc.

10. A device as in claim 1, wherein the device has a specific gravity of between 0.25 and 4.0.

11. A device as in claim 1, wherein the device has an overall cross-sectional shape selected from the group consisting of a circle, an ellipse, a triangle, a diamond, a rectangle, a square, a star of a combination thereof.

12. A device as in claim 1, wherein the device is cone-shaped, with the tissue engagement portion disposed toward an apex of the cone and the support portion disposed toward a base of the cone.

13. A device as in claim 1, wherein the outer shell comprises a material selected from the group consisting of silicone, polyeurethane and polyethylene.

14. A device as in claim 13, wherein the outer shell is movable from the first configuration to the second configuration by applying force to the shell with a distal end of an elongate catheter device.

15. A device as in claim 13, wherein the inner plug is solid.

16. A device as in claim 1, wherein the retaining member self-expands from a first configuration to a second configuration.

17. A device as in claim 16, wherein the retaining member is adapted to expand within the stomach.

18. A device as in claim 1, wherein a cross-sectional diameter of the retaining member is smaller than a cross-sectional diameter of the support portion in the second configuration.

19. A device as in claim 18, wherein the cross-sectional diameter of the retaining member is about 30 mm or less.

20. A device as in claim 1, wherein the retaining member includes at least one hole, ring, or loop for attaching a removal device.

21. A device as in claim 1, wherein the positioning member has a length of at least 3.0 cm.

22. A device as in claim 1, wherein the positioning member has a cross-sectional diameter of 2 cm or less.

23. A device as in claim 1, wherein the shape of the positioning member is further adapted to permit the device to intermittently move into and out of contact with the pyloric valve.

24. A device as in claim 1, wherein the positioning member is adapted to self-expand from a first diameter to a larger second diameter within the pyloric valve.

25. A device as in claim 1, wherein the device is deliverable into the stomach through an esophagus with the support portion in the first configuration.

26. A device as in claim 25, wherein the device is removably couplable with an elongate device for delivery of the device to the stomach through the esophagus.

27. A device as in claim 25, wherein the device is adapted to be delivered through a lumen of a tube extending from a mouth through the esophagus into the stomach.

28. A device as in claim 25, wherein the support portion is collapsible from the second configuration to the first configuration for removal of the device through the esophagus.

29. A device as in claim 25, wherein the device comprises one or more biodegradable materials so as to degrade over time and pass through the pyloric valve and the rest of a digestive system.

30. A device as in claim 29, wherein the biodegradable materials are selected from the group consisting of cellulose, polyethylene glycol, collagen, and polylactic acid.

31. A device for obstructing a pyloric valve of a stomach, the device comprising:
  an obstructing member adapted to reconfigure in the stomach from a first configuration to a larger second configuration which is sized to prevent passage of the device through the pyloric valve, wherein the obstructing member presents a surface comprising a compliant outer shell when in the larger second configuration which surrounds an inner plug within a hollow portion formed within the obstructing member and which intermittently engages stomach tissue adjacent the pyloric valve whereby the pyloric valve is intermittently obstructed;
  a tubular positioning member having a length extending from the obstructing member, the positioning member having a shape adapted to pass at least partially through the pyloric valve to position the obstructing member over the pyloric valve, where the outer shell is movable from a first configuration in which it overlaps at least part of the positioning member to a second configuration in which it overlaps at least part of the plug; and,
  a retaining member having a diameter larger than the positioning member and coupled with a distal end of the positioning member for maintaining the device in intermittent contact with the pyloric valve, where the retaining member has an atraumatic shape.

32. A device as in claim 31, wherein the obstructing member self-expands from the first configuration to the second configuration.

33. A device as in claim 31, wherein the outer shell comprises a material selected from the group consisting of silicone, polyurethane and polyethylene.

34. A device as in claim 33, wherein the outer shell is movable from the first configuration to the second configuration by applying force to the shell with a distal end of an elongate catheter device.

35. A device as in claim 33, wherein the inner plug is solid.

36. A device as in claim 31, wherein the retaining member self-expands from a first configuration to a second configuration.

37. A system for obstructing a pyloric valve of a stomach, the system comprising:
  a pyloric valve obstructing device comprising:
    an expandable support portion adapted to reconfigure in the stomach from a first configuration to a larger second configuration, wherein the support portion in the second configuration is sized to prevent passage of the device through the pyloric valve;
    a compliant tissue engagement surface comprising a compliant outer shell which is formed external to the expandable support portion when in the larger second configuration such that the surface surrounds an inner plug within a hollow portion formed within the support portion and wherein the surface is adapted to be intermittently engaged to stomach tissue adjacent the pyloric valve whereby the pyloric valve is intermittently obstructed; and,
    a tubular retaining member having a length coupled to the tissue engagement surface where the retaining member has an atraumatic shape, where the outer shell is movable from a first configuration in which it overlaps at least part of the retaining member to a second configuration in which it overlaps at least part of the plug; and
  a delivery device attachable to a coupling feature along the obstructing device for delivering the pyloric valve obstructing device to the stomach through an esophagus.

38. A system as in claim 37, wherein the support portion is adapted to self-expand from the first configuration to the second configuration within the stomach.

39. A system as in claim 37, wherein the delivery device comprises an elongate flexible catheter.

40. A system as in claim 39, wherein the flexible catheter defines a lumen in which the obstructing device is housed during delivery.

41. A system as in claim 40, wherein the flexible catheter further comprises a coupling mechanism for releasably holding the obstructing device within the lumen during delivery.

42. A system as in claim 41, wherein the delivery device is adapted to remove the obstructing device from the stomach through the esophagus.

43. A system as in claim 37, wherein the obstructing device comprises one or more biodegradable materials so as to degrade over time and pass through the pyloric valve and the rest of a digestive system.

44. A system as in claim 43, wherein the biodegradable materials are selected from the group consisting of cellulose, polyethylene glycol, collagen, and polylactic acid.

* * * * *